US008999702B2

(12) United States Patent
Kelly, Jr. et al.

(10) Patent No.: US 8,999,702 B2
(45) Date of Patent: Apr. 7, 2015

(54) STIRRED TANK BIOREACTOR

(75) Inventors: James E. Kelly, Jr., Melrose, MA (US); Joseph William Muldoon, West Boylston, MA (US); Stephen Proulx, Boxboro, MA (US); James Vigna, North Andover, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 12/387,688

(22) Filed: May 6, 2009

(65) Prior Publication Data
US 2009/0311776 A1    Dec. 17, 2009

Related U.S. Application Data

(60) Provisional application No. 61/131,640, filed on Jun. 11, 2008.

(51) Int. Cl.
C12M 1/00       (2006.01)
C12M 1/02       (2006.01)
C12M 3/00       (2006.01)

(52) U.S. Cl.
CPC ............ C12M 23/28 (2013.01); *C12M 23/48* (2013.01); C12M 23/20 (2013.01); C12M 27/00 (2013.01)

(58) Field of Classification Search
CPC ...... C12M 23/20; C12M 27/00; C12M 23/28; C12M 23/48
USPC ...................................... 435/289.1
See application file for complete search history.

(56) References Cited

U.S. PATENT DOCUMENTS 3,556,302 A    1/1971    Agranat
3,565,973 A    2/1971    Michaels et al.
(Continued)

FOREIGN PATENT DOCUMENTS

EP       0003089 B1    8/1981
EP       0162034 B1    11/1990
(Continued)

OTHER PUBLICATIONS

Extended European Search Report received for EP Patent Application No. 09161982.5, mailed on Nov. 17, 2009, 6 pages.
(Continued)

*Primary Examiner* — Nathan Bowers
*Assistant Examiner* — Gautam Prakash
(74) *Attorney, Agent, or Firm* — EMD Millipore Corporation

(57) ABSTRACT

The present invention is a disposable bioreactor formed of molded plastic. The bioreactor is presterilized and has a top and body sealed to each other. One or more ports are formed in the top and side of the housing. Preferably at least one port is below the liquid/air level for the housing. The one or more ports that are below the liquid/air interface level may be used as sampling ports or access ports for probes or drains or supply ports for liquids or gases. The bioreactor provides a direct retrofit for the existing glass or steel assembly that utilizes the existing support structures and controls. The molded design overcomes issues of discontinuity, dead spots and the like due to its fixed dimensions that are built in by the molding process. Reproducible probe and other equipment location is also guaranteed through the use of the molded port features. The molded plastic allows for greater flexibility in material selection to reduce or eliminate lipid or cholesterol binding.

4 Claims, 12 Drawing Sheets

(56) References Cited

U.S. PATENT DOCUMENTS

| | | | |
|---|---|---|---|
| 3,632,507 | A | 1/1972 | Witt et al. |
| 3,702,806 | A | 11/1972 | Oliva |
| 3,737,377 | A | 6/1973 | Sternberg et al. |
| 3,859,212 | A | 1/1975 | Smalley et al. |
| 3,968,037 | A | 7/1976 | Morgan et al. |
| 4,045,377 | A | 8/1977 | Pearson |
| 4,055,469 | A | 10/1977 | Snoke et al. |
| 4,200,695 | A | 4/1980 | Chong et al. |
| 4,305,829 | A | 12/1981 | Kelsey et al. |
| 4,359,537 | A | 11/1982 | Chong |
| 4,371,674 | A | 2/1983 | Hertel et al. |
| 4,380,590 | A | 4/1983 | Chong |
| 4,382,028 | A | 5/1983 | Paget |
| 4,515,893 | A | 5/1985 | Kung et al. |
| 4,536,294 | A | 8/1985 | Guillet et al. |
| 4,676,980 | A | 6/1987 | Segal et al. |
| 4,780,409 | A | 10/1988 | Monji et al. |
| 4,816,567 | A | 3/1989 | Cabilly et al. |
| 4,828,701 | A | 5/1989 | Cussler |
| 4,839,046 | A | 6/1989 | Chandler |
| 4,863,613 | A | 9/1989 | Johnson et al. |
| 4,904,385 | A | 2/1990 | Wessling et al. |
| 4,912,032 | A | 3/1990 | Hoffman et al. |
| 4,925,785 | A | 5/1990 | Wang et al. |
| 4,968,435 | A | 11/1990 | Neff et al. |
| 5,003,047 | A | 3/1991 | Yarmush et al. |
| 5,047,511 | A | 9/1991 | Mehrotra |
| 5,091,178 | A | 2/1992 | Hellstrom et al. |
| 5,091,313 | A | 2/1992 | Chang |
| 5,152,903 | A | 10/1992 | Neff et al. |
| 5,164,057 | A | 11/1992 | Mori et al. |
| 5,171,450 | A | 12/1992 | Hoots |
| 5,238,545 | A | 8/1993 | Yoshioka et al. |
| 5,258,122 | A | 11/1993 | Ha et al. |
| 5,324,787 | A | 6/1994 | Pinschmidt, Jr. et al. |
| 5,340,865 | A | 8/1994 | Neff et al. |
| 5,354,481 | A | 10/1994 | Neff et al. |
| 5,354,801 | A | 10/1994 | O'Toole |
| 5,374,971 | A * | 12/1994 | Clapp et al. .......... 348/376 |
| 5,430,110 | A | 7/1995 | Ahlers et al. |
| 5,512,480 | A * | 4/1996 | Sandstrom et al. ...... 435/289.1 |
| 5,573,675 | A | 11/1996 | Sommese et al. |
| 5,599,719 | A | 2/1997 | Woiszwillo et al. |
| 5,622,700 | A | 4/1997 | Jardieu et al. |
| 5,672,347 | A | 9/1997 | Aggarwal et al. |
| 5,684,107 | A | 11/1997 | Schneider et al. |
| 5,693,762 | A | 12/1997 | Queen et al. |
| 5,714,338 | A | 2/1998 | Wai Fei et al. |
| 5,721,108 | A | 2/1998 | Robinson et al. |
| 5,725,856 | A | 3/1998 | Hudziak et al. |
| 5,736,137 | A | 4/1998 | Anderson et al. |
| 5,739,383 | A | 4/1998 | Yoon et al. |
| 5,770,358 | A | 6/1998 | Dower et al. |
| 5,807,489 | A | 9/1998 | Farinato et al. |
| 5,840,804 | A | 11/1998 | Carl et al. |
| 5,840,851 | A | 11/1998 | Plomer et al. |
| 5,879,564 | A | 3/1999 | Farinato |
| 5,929,214 | A | 7/1999 | Peters et al. |
| 5,994,560 | A | 11/1999 | Yoon et al. |
| 5,998,588 | A | 12/1999 | Hoffman et al. |
| 6,024,955 | A | 2/2000 | Asano et al. |
| 6,127,526 | A | 10/2000 | Blank |
| 6,133,047 | A | 10/2000 | Elaissari et al. |
| 6,139,746 | A | 10/2000 | Kopf |
| 6,147,176 | A | 11/2000 | Neff et al. |
| 6,191,242 | B1 | 2/2001 | Ryles et al. |
| 6,197,522 | B1 | 3/2001 | Keller et al. |
| 6,245,555 | B1 | 6/2001 | Curtis |
| 6,258,275 | B1 | 7/2001 | Freitag et al. |
| 6,294,622 | B1 | 9/2001 | Barajas et al. |
| 6,307,013 | B1 | 10/2001 | Chivers |
| 6,358,730 | B1 | 3/2002 | Kane |
| 6,367,749 | B2 * | 4/2002 | Valiulis ............ 248/188 |
| 6,372,141 | B1 | 4/2002 | Okano et al. |
| 6,420,487 | B1 | 7/2002 | Vaidya et al. |
| 6,454,950 | B1 | 9/2002 | Tjerneld et al. |
| 6,521,341 | B1 | 2/2003 | Elaissari et al. |
| 6,534,633 | B1 | 3/2003 | Weidanz et al. |
| 6,538,089 | B1 | 3/2003 | Samra et al. |
| 6,544,424 | B1 | 4/2003 | Shevitz |
| 6,565,872 | B2 | 5/2003 | Wu et al. |
| 6,582,926 | B1 | 6/2003 | Chilkoti |
| 6,638,918 | B2 | 10/2003 | Davison et al. |
| 6,641,735 | B1 | 11/2003 | Yoshizako et al. |
| 6,673,598 | B1 | 1/2004 | Akers et al. |
| 6,689,836 | B2 | 2/2004 | Vaidya et al. |
| 6,706,187 | B1 | 3/2004 | Okano et al. |
| 6,709,862 | B2 | 3/2004 | Curtis |
| 6,737,235 | B1 | 5/2004 | Cros et al. |
| 6,765,081 | B2 | 7/2004 | Lin et al. |
| 6,770,758 | B2 | 8/2004 | Pan et al. |
| 6,805,793 | B2 | 10/2004 | Yoshizako et al. |
| 6,821,515 | B1 | 11/2004 | Cleland et al. |
| 6,830,670 | B1 | 12/2004 | Viovy et al. |
| 6,852,819 | B2 | 2/2005 | Ohnishi et al. |
| 6,858,694 | B2 | 2/2005 | Ohnishi et al. |
| 6,863,437 | B2 | 3/2005 | Ohnishi et al. |
| 6,867,268 | B2 | 3/2005 | Vaidya et al. |
| 6,926,832 | B2 | 8/2005 | Collins et al. |
| 6,956,077 | B1 | 10/2005 | Akiyama et al. |
| 6,967,085 | B1 | 11/2005 | Hughes et al. |
| 6,974,660 | B2 | 12/2005 | Manias et al. |
| 7,001,953 | B2 | 2/2006 | Chen et al. |
| 7,011,930 | B2 | 3/2006 | Manias et al. |
| 7,012,136 | B2 | 3/2006 | Yamanaka et al. |
| 7,052,917 | B1 | 5/2006 | Ohnishi et al. |
| 7,070,696 | B2 | 7/2006 | Weir et al. |
| 7,083,948 | B1 | 8/2006 | Sassenfeld et al. |
| 7,157,603 | B2 | 1/2007 | Hilbrig |
| 7,160,971 | B2 | 1/2007 | Mallapragada et al. |
| 7,169,908 | B2 | 1/2007 | Lester et al. |
| 7,195,925 | B2 | 3/2007 | Ohnishi et al. |
| 7,300,545 | B2 | 11/2007 | Ohara et al. |
| 7,355,020 | B2 | 4/2008 | Yamanaka et al. |
| 7,377,686 | B2 | 5/2008 | Hubbard |
| 7,393,698 | B2 | 7/2008 | Furukawa et al. |
| 7,422,724 | B1 | 9/2008 | Manginell et al. |
| 7,429,458 | B2 | 9/2008 | Chilkoti |
| 7,442,515 | B2 | 10/2008 | Ratner et al. |
| 7,514,007 | B2 | 4/2009 | Chen et al. |
| 7,541,167 | B2 | 6/2009 | Dave et al. |
| 7,547,747 | B2 | 6/2009 | Hashimoto et al. |
| 7,553,658 | B2 | 6/2009 | Kepka et al. |
| 7,625,764 | B2 | 12/2009 | Stayton et al. |
| 7,632,656 | B2 | 12/2009 | Kanazawa et al. |
| 7,695,905 | B2 | 4/2010 | Furukawa et al. |
| 7,767,399 | B2 | 8/2010 | Murphy et al. |
| 8,163,886 | B2 | 4/2012 | Moya |
| 2002/0058786 | A1 | 5/2002 | Chivers |
| 2002/0098567 | A1 | 7/2002 | Vaidya et al. |
| 2003/0059840 | A1 | 3/2003 | Chilkoti |
| 2003/0186293 | A1 | 10/2003 | Ohnishi et al. |
| 2004/0010163 | A1 | 1/2004 | Hilbrig |
| 2004/0039177 | A1 | 2/2004 | Yamanaka et al. |
| 2004/0062140 | A1 * | 4/2004 | Cadogan et al. ............ 366/144 |
| 2004/0134846 | A1 | 7/2004 | Akiyama et al. |
| 2005/0016620 | A1 | 1/2005 | Proulx et al. |
| 2005/0063259 | A1 | 3/2005 | Isshiki et al. |
| 2005/0158782 | A1 | 7/2005 | Furukawa et al. |
| 2005/0158851 | A1 * | 7/2005 | Furey .................. 435/289.1 |
| 2005/0175702 | A1 | 8/2005 | Muller-Schulte |
| 2005/0224415 | A1 | 10/2005 | Akiyama et al. |
| 2005/0272146 | A1 | 12/2005 | Hodge et al. |
| 2005/0282169 | A1 | 12/2005 | Turner et al. |
| 2006/0121519 | A1 | 6/2006 | Patchornik |
| 2006/0162882 | A1 | 7/2006 | Ohara et al. |
| 2006/0189795 | A1 | 8/2006 | Van Alstine et al. |
| 2006/0251610 | A1 | 11/2006 | Nakahama |
| 2006/0281158 | A1 * | 12/2006 | Felder et al. ............... 435/168 |
| 2007/0148437 | A1 | 6/2007 | Muller-Schulte |
| 2007/0193954 | A1 | 8/2007 | Busson |
| 2007/0224241 | A1 | 9/2007 | Stayton et al. |
| 2007/0249737 | A1 * | 10/2007 | Miller et al. ............... 518/700 |
| 2008/0032396 | A1 * | 2/2008 | Chokshi .................. 435/294.1 |

(56) References Cited

U.S. PATENT DOCUMENTS

| | | |
|---|---|---|
| 2008/0131957 A1 | 6/2008 | Ryan et al. |
| 2008/0160559 A1 | 7/2008 | Carre et al. |
| 2008/0193981 A1 | 8/2008 | Fahrner et al. |
| 2008/0220531 A1 | 9/2008 | Stayton et al. |
| 2008/0255027 A1 | 10/2008 | Moya et al. |
| 2008/0284163 A1 | 11/2008 | Proulx et al. |
| 2008/0293118 A1 | 11/2008 | Furukawa et al. |
| 2008/0293926 A1 | 11/2008 | Hallgren et al. |
| 2009/0001025 A1 | 1/2009 | Takahashi et al. |
| 2009/0036651 A1 | 2/2009 | Moya |
| 2009/0148961 A1 | 6/2009 | Luchini et al. |
| 2009/0155201 A1 | 6/2009 | Mandeville, III et al. |
| 2009/0232737 A1 | 9/2009 | Moya et al. |
| 2009/0233327 A1 | 9/2009 | Lau et al. |
| 2010/0190963 A1 | 7/2010 | Moya et al. |
| 2010/0193148 A1 | 8/2010 | McKay et al. |
| 2010/0267933 A1 | 10/2010 | Wilson |
| 2010/0282425 A1 | 11/2010 | Karppi et al. |
| 2011/0020327 A1 | 1/2011 | Moya et al. |
| 2011/0313066 A1 | 12/2011 | Jaber et al. |
| 2012/0070836 A1 | 3/2012 | Zillmann et al. |

FOREIGN PATENT DOCUMENTS

| | | |
|---|---|---|
| EP | 0534016 A1 | 3/1993 |
| EP | 0420937 B1 | 11/1994 |
| EP | 0922715 A2 | 6/1999 |
| EP | 0922715 A3 | 11/2003 |
| EP | 1923461 | 5/2008 |
| GB | 2305936 | 4/1997 |
| KR | 10-2009-0113264 A | 10/2009 |
| WO | 91/00360 A1 | 1/1991 |
| WO | 92/20373 A1 | 11/1992 |
| WO | 93/04173 A1 | 3/1993 |
| WO | 93/04713 A1 | 3/1993 |
| WO | 93/08829 A1 | 5/1993 |
| WO | 93/14110 A1 | 7/1993 |
| WO | 93/16185 A2 | 8/1993 |
| WO | 94/15951 A1 | 7/1994 |
| WO | 95/06249 A1 | 3/1995 |
| WO | 95/19181 A1 | 7/1995 |
| WO | 95/23865 A1 | 9/1995 |
| WO | 96/02577 A1 | 2/1996 |
| WO | 96/27011 A1 | 9/1996 |
| WO | 96/30046 A1 | 10/1996 |
| WO | 96/40210 A1 | 12/1996 |
| WO | 97/26912 A2 | 7/1997 |
| WO | 98/06248 A2 | 2/1998 |
| WO | 98/23761 A1 | 6/1998 |
| WO | 98/33162 A1 | 7/1998 |
| WO | 98/45331 A2 | 10/1998 |
| WO | 98/51793 A1 | 11/1998 |
| WO | 99/01556 A2 | 1/1999 |
| WO | 00/12618 A1 | 3/2000 |
| WO | 00/46262 A1 | 8/2000 |
| WO | 00/67901 A1 | 11/2000 |
| WO | 00/75348 A1 | 12/2000 |
| WO | 01/07548 A1 | 2/2001 |
| WO | 01/40309 A2 | 6/2001 |
| WO | 2004/056312 A2 | 7/2004 |
| WO | 2004/092393 A1 | 10/2004 |
| WO | 2005/010141 A2 | 2/2005 |
| WO | 2005/021129 A1 | 3/2005 |
| WO | WO 2005/108546 | 11/2005 |
| WO | WO 2005/118771 | 12/2005 |
| WO | 2006/085321 A2 | 8/2006 |
| WO | WO 2006/138143 | 12/2006 |
| WO | 2007/002690 A1 | 1/2007 |
| WO | 2007/038523 A2 | 4/2007 |
| WO | 2007/073311 A1 | 6/2007 |
| WO | 2007/104456 A1 | 9/2007 |
| WO | 2007/148230 A2 | 12/2007 |
| WO | 2008/004988 A1 | 1/2008 |
| WO | 2008/079280 A1 | 7/2008 |
| WO | 2008/079302 A2 | 7/2008 |
| WO | 2008/091740 A2 | 7/2008 |
| WO | 2008/097154 A1 | 8/2008 |
| WO | 2009/089570 A1 | 7/2009 |
| WO | 2009/141664 A1 | 11/2009 |
| WO | 2009/158606 A2 | 12/2009 |
| WO | 2010/082894 A1 | 7/2010 |

OTHER PUBLICATIONS

International Search Report and Written Opinion received for PCT Patent Application No. PCT/US2009/002787, mailed on Nov. 12, 2009, 9 pages.
International Preliminary Report on Patentability received for PCT Patent Application No. PCT/US2009/002787, issued on Dec. 13, 2010, 6 pages.
Lehermayr et al., "Assessment of Net Charge and Protein-Protein Interactions of Different Monoclonal Antibodies", Journal of Pharmaceutical Sciences, vol. 100, No. 7, Jul. 2011, pp. 2551-2562.
Anastase-Ravion et al., "New Antibody Purification Procedure using a Thermally Responsive Poly(N-Isopropylacrylamide)—Dextran Derivative Conjugate", Journal of Chromatography B: Biomedical Sciences and Applications, vol. 761, No. 2, Sep. 25, 2001, pp. 247-254.
Aruffo et al., "CD44 is the Principal Cell Surface Receptor for Hyaluronate", Cell, vol. 61, No. 7, Jun. 29, 1990, pp. 1303-1313.
Ayano et al., "Aqueous Chromatography System Using pH- and Temperature-Responsive Stationary Phase with Ion-Exchange Groups", Journal of Chromatography A, vol. 1119, Jun. 30, 2006, pp. 58-65.
Brennan et al., "Preparation of Bispecific Antibodies by Chemical Recombination of Monoclonal Immunoglobulin G1 Fragments", Science, vol. 229, Jul. 5, 1985, pp. 81-83.
Brodeur et al., "Monoclonal Antibody Production Techniques and Applications", Marcel Dekker Inc., New York, 1987, pp. 51-63.
Brüggemann et al., "Designer Mice: The Production of Human Antibody Repertoires in Transgenic Animals", The Year in Immunology, vol. 7, 1993, pp. 33-40.
Carter et al., "High Level *Escherichia coli* Expression and Production of a Bivalent Humanized Antibody Fragment", Nature Biotechnology, vol. 10, 1992, pp. 163-167.
Carter et al., "Highly Branched Stimuli Responsive Poly[(N-isopropyl acrylamide)-co-(1,2-propandiol-3-methacrylate)]s with Protein Binding Functionality", Macromolecular Bioscience, vol. 5, No. 5, May 23, 2005, pp. 373-378.
Carter et al., "Humanization of an Anti-p185HER2 Antibody for Human Cancer Therapy", Proc. Natl. Acad. Sci. USA, vol. 89, May 1992, pp. 4285-4289.
Cellseed Inc., "Technology: Temperature-Responsive Polymers", Document Retrieved on Oct. 13, 2010, available online at: <http://www.cellseed.com/technology-e/index.html>, 1 page.
Ceriani et al., "Biological Activity of Two Humanized Antibodies against Two Different Breast Cancer Antigens and Comparison to their Original Murine Forms", Cancer Research (Suppl.), vol. 55, Dec. 1, 1995, pp. 5852s-5856s.
Chen et al., "A New Temperature- and pH-Responsive Copolymer for Possible Use in Protein Conjugation", Macromolecular Chemistry and Physics, vol. 196, No. 4, Apr. 1995, pp. 1251-1259.
Chen et al., "Graft Copolymers that Exhibit Temperature-Induced Phase Transitions Over a Wide Range of pH", Nature, vol. 373, No. 5, Jan. 5, 1995, pp. 49-52.
Chen et al., "pH-Dependence of the Properties of Hydrophobically Modified Polyvinylamine", Langmuir, vol. 21, No. 25, 2005, pp. 11673-11677.
Chen et al., "Polymer-protein conjugates. II. Affinity precipitation separation of human immunogammaglobulin by a poly(N-isopropylacrylamide)-protein A conjugate", Biomaterials, vol. 11, No. 9, 1990, pp. 631-634.
Chern et al., "Characterization of pH-sensitive polymeric supports for selective precipitation of proteins", Colloids and Surfaces B: Biointerfaces vol. 6, 1996, pp. 37-49.

(56) References Cited

OTHER PUBLICATIONS

Chothia et al., "Canonical Structures for the Hypervariable Regions of Immunoglobulins", Journal of Molecular Biology, vol. 196, No. 4, Aug. 20, 1987, pp. 901-917.
Choy et al., "Percentage of anti-CD4 monoclonal antibody-coated lymphocytes in the rheumatoid joint is associated with clinical improvement. Implications for the development of immunotherapeutic dosing regimens", Arthritis & Rheumatism, vol. 39, No. 1, Jan. 1996, pp. 52-56.
Clackson et al., "Making antibody fragments using phage display libraries", Nature, vol. 352, Aug. 15, 1991, pp. 624-628.
Dainiak et al., "Affinity precipitation of monoclonal antibodies by nonstoichiometric polyelectrolyte complexes", Bioseparation, vol. 7, No. 4-5 (Abstract Only supplied), Jul. 1, 1999, pp. 231-240.
Deng et al., "Temperature-Sensitive Flocculants Based on Poly(N-isopropylacrylamide-co-diallyldimethylammonium Chloride)", Journal of Colloid and Interface Science, vol. 179, No. 1, Apr. 15, 1996, pp. 188-193.
Dhainaut et al., "CDP571, A Humanized Antibody to Human Tumor Necrosis Factor-Alpha: Safety, Pharmacokinetics, Immune Response, and Influence of the Antibody on Cytokine Concentrations in Patients with Septic Shock", Critical Care Medicine, vol. 23, No. 9, Sep. 1995, pp. 1461-1469.
Ding et al., "Size-dependent control of the binding of biotinylated proteins to streptavidin using a polymer shield", Nature, vol. 411, May 3, 2001, pp. 59-62.
Duchosal et al., "Immunization of hu-PBL—SCID mice and the rescue of human monoclonal Fab fragments through combinatorial libraries", Nature, vol. 355, Jan. 16, 1992, pp. 258-262.
Eisenberg et al., "Viscosities of dilute aqueous solutions of a partially quaternized poly-4-vinylpyridine at low gradients of flow", Journal of Polymer Science, vol. 13, No. 68, Feb. 1954, pp. 85-91.
Ellis et al., "Engineered anti-CD38 monoclonal antibodies for immunotherapy of multiple myeloma", The Journal of Immunology, vol. 155, No. 2, 1995, pp. 925-937.
Eriksson et al., "Flocculation of *E. coli* Bacterial With Cationic Polyelectrolytes", Flocculation in Biotechnology and Separation Systems, 1987, pp. 441-455.
Esser et al., "Genetic Control of Flocculation of Yeast With Respect to Application in Biotechnology", Flocculation in Biotechnology and Separation Systems, 1987, pp. 383-389.
Ferreira et al., "Purification of human immunoglobulin G by thermoseparating aqueous two-phase systems", Journal of Chromatography A, vol. 1195, 2008, pp. 94-100.
Fong et al., "Affinity Separation Using an Fv Antibody Fragment—"Smart" Polymer Conjugate", BioTechnology and BioEngineenng, vol. 79, No. 3, Aug. 5, 2002, pp. 271-276.
Fong et al., "Thermoprecipitation of Streptavidin via Oligonucleotide-Mediated Self-Assembly with Poly(N-isopropylacryalminde)", Bioconjugate Chem., vol. 10, 1999, pp. 720-725.
Freitag et al., "Stimulus-Responsive Polymers for Bioseparation", Chimia, vol. 55, No. 3, 2001, pp. 196-200.
Galaev, I Yu, "'Smart' polymers in biotechnology and medicine", Russian Chemical Reviews, vol. 64 No. 5, 1995, pp. 471-489.
Garret-Flaudy et al., "Use of the Avidin (Imino) biotin System as a General Approach to Affinity Precipitation", BioTechnology and BioEngineering, vol. 71, No. 3, 2000/2001, pp. 223-234.
Gawande et al., "Purification of *Aspergillus* sp xylanase by precipitation with an anionic polymer Eudragit S100", Process Biochemistry, vol. 34, No. 6-7, Sep. 1999, pp. 577-580.
Gil et al., "Stimuli-reponsive polymers and their bioconjugates", Progress in Polymer Science, vol. 29, No. 12, Dec. 2004, pp. 1173-1222.
Goding, James W., "Monoclonal Antibodies: Principles and Practice", Academic Press. 1986, pp. 59-103.
Graziano et al., "Construction and characterization of a humanized anti-gamma-Ig receptor type I (Fc gamma RI) monoclonal antibody", The Journal of Immunology, vol. 155, No. 10, 1995, pp. 4996-5002.
Gruber et al., "Efficient tumor cell lysis mediated by a bispecific single chain antibody expressed in *Escherichia coli*", The Journal of Immunology, vol. 152, No. 11, 1994, pp. 5368-5374.
Guoqiang et al., "Alternative modes of precipitation of Eudragit S-100: a potential ligand carrier for affinity precipitation of protein", Bioseparation, vol. 5, 1995, pp. 339-350.
Gupta et al., "Affinity Precipitation of Proteins", Journal of Molecular Recognition, vol. 9, 1996, pp. 356-359.
Han et al., "Flocculation of biological cells: Experiment vs. theory", AIChE Journal, vol. 49, No. 7, Jul. 2003, pp. 1687-1701.
Hayashi et al., "Capturing of acidic macromolecules from biological samples using a temperature-responsive polymer modified with poly-L-lysine", Analyst, vol. 129, 2004, pp. 421-427.
Hilbrig et al., "Protein purification by affinity precipitation", Journal of Chromatography B: Biomedical Sciences and Applications, vol. 790, Jun. 25, 2003, pp. 79-90.
Holliger et al., "Diabodies: small bivalent and bispecific antibody fragments", The Proceedings of the National Academy of Sciences, USA, vol. 90, No. 14., Jul. 15, 1993, pp. 6444-6448.
Hoogenboom et al., "By-passing immunisation : Human antibodies from synthetic repertoires of germline VH gene segments rearranged in vitro", Journal of Molecular Biology, vol. 227, No. 2, Sep. 20, 1992, pp. 381-388.
Hoogenboom et al., "Construction and expression of antibody-tumor necrosis factor fusion proteins", Molecular Immunology, vol. 28, No. 9, Sep. 1991, pp. 1027-1037.
Hoshino et al., "Preparation of a New Thermo-Responsive Adsorbent with Maltose as a Ligand and Its Application to Affinity Precipitation", BioTechnology and BioEngineering, vol. 60, No. 5, Dec. 5, 1998, pp. 568-579.
Zuker, Michael, "Mfold web server for nucleic acid folding and hybridization prediction", Nucleic Acids Research, vol. 31, No. 13, Jul. 1, 2003, pp. 3406-3415.
Hourmant et al., "Administration of an anti-CD11a monoclonal antibody in recipients of kidney transplantation. A pilot study", Transplantation, vol. 58, No. 3, 1994, pp. 377-380.
Hughes et al., "The flocculation of bacteria using cationic synthetic flocculants and chitosan", Biotechnology Techniques, vol. 4, No. 1, 1990, pp. 55-60.
Izumrudov et al., "Polycomplexes—potential for bioseparation", Bioseparation, vol. 7, 1999, pp. 207-220.
Jakobovits et al., "Analysis of homozygous mutant chimeric mice: Deletion of the immunoglobulin heavy-chain joining region blocks B-cell development and antibody production", Proc. Natl. Acad. Sci. USA, vol. 90, Mar. 1993, pp. 2551-2555.
Jakobovits et al., "Germ-line transmission and expression of a human-derived yeast artificial chromosome", Nature, vol. 362, Mar. 18, 1993, pp. 255-258.
Jones et al., "Replacing the complementarity-determining regions in a human antibody with those from a mouse", Nature, vol. 321, May 29, 1986, pp. 522-525.
Jurcic et al., "Radiolabeled Anti-CD33 Monoclonal Antibody M195 for Myeloid Leukemias", Cancer Research (Suppl.), vol. 55., Dec. 1, 1995, pp. 5908s-5910s.
Juweid et al., "Treatment of Non-Hodgkin's lymphoma with radiolabeled murine, chimeric, or humanized LL2, an anti-CD22 monoclonal antibody", Cancer Research (Suppl.), vol. 55, Dec. 1, 1995, pp. 5899s-5907s.
Kamihira et al., "Purification of recombinant protein A by aqueous two-phase extraction integrated with affinity precipitation", Biotechnology and Bioengineering, vol. 40, No. 11, Dec. 1992, pp. 1381-1387.
Kanazawa et al., "Temperature-responsive liquid chromatography. 2. Effects of hydrophobic groups in N-isopropylacrylamide copolymer-modified silica", Anal Chem., vol. 69, No. 5, 1997, pp. 823-830.
Kanazawa et al., "Temperature-responsive stationary phase utilizing a polymer of proline derivative for hydrophobic interaction chromatography using an aqueous mobile phase", Journal of Chromatography A, vol. 1106, Feb. 17, 2006, pp. 152-158.
Karim et al., "Flocculation enhanced microfiltration of *Escherichia coli* lysate", Biochemical Engineering Journal, vol. 40, No. 3, Jul. 1, 2008, pp. 512-519.

(56) References Cited

OTHER PUBLICATIONS

Kim et al., "Flocculation to enhance microfiltration", Journal of Membrane Science, vol. 182, No. 1-2, Feb. 15, 2001, pp. 161-172.
Kim et al., "Removal of Cell and Cell Debris by Electrostatic Adsorption of Positively Charged Polymeric Particles", Flocculation in Biotechnology and Separation Systems, 1987, pp. 429-439.
Kim et al., "The vascular endothelial growth factor proteins: identification of biologically relevant regions by neutralizing monoclonal antibodies", Growth Factors, vol. 7, 1992, pp. 53-64.
Kohler et al., "Continuous cultures of fused cells secreting antibody of predefined specificity", Nature, vol. 256 (Attached version of document is reprinted with permission in the Journal of Immunology, 2005, vol. 174, pp. 2453-2455)., Aug. 7, 1975, pp. 495-497.
Kostelny et al., "Formation of a bispecific antibody by the use of leucine zippers", The Journal of Immunology, vol. 148, No. 5, 1992, pp. 1547-1553.
Kozbor et al., "A human hybrid myeloma for production of human monoclonal antibodies", The Journal of Immunology, vol. 133, No. 6, 1984, pp. 3001-3005.
Kumar et al., Isolation and Purification of Proteins, edited by Rajni Hatti-Kaul et al., 2003, pp. 236-275.
Kumar et al., "Affinity precipitation of α-amylase inhibitor from wheat meal by metal chelate affinity binding using Cu (II)-loaded copolymers of 1-vinylimidazole with N-isopropylacrylamide", Biotechnology and Bioengineering, vol. 59, No. 6, 1998, pp. 695-704.
Kumar et al., "Smart Polymers: Physical Forms and Bioengineering Applications", Prog. Polym. Sci., vol. 32, 2007, pp. 1205-1237.
Kumar et al., "Type-Specific Separation of animal cells in an aqueous two-phase systems using antibody conjugates with temperature-sensitive polymers", Biotechnology and Bioengineering, vol. 75, No. 5, Dec. 5, 2001, pp. 570-580.
Ladisch et al., "Scale-Up of Bioseparations for Microbial and Biochemical Technology", ACS Symposium Series, vol. 362, Chapter 7, 1988, pp. 72-101.
Laemmli, U. K., "Cleavage of structural proteins during the assembly of the head of bacteriophage T4", Nature, vol. 227, No. 5259, Aug. 15, 1970, pp. 680-685.
Larsson et al., "Evaluation of affinity precipitation and a traditional affinity Chromatographic procedure for purification of soybean lectin, from extracts of soya flour", Journal of Biotechnology, vol. 49, No. 1-3, Aug. 20, 1996, pp. 189-199.
Li et al., "Effect of molecular weight of poly(N-isopropyl acrylamide) temperature-sensitive flocculants on dewatering", AIChE Journal, vol. 55, No. 8, Aug. 2009, pp. 2070-2080.
Litton et al., "Antibody-targeted superantigen therapy induces tumor-infiltrating lymphocytes, excessive cytokine production, and apoptosis in human colon carcinoma", European Journal of Immunology, vol. 26, No. 1, Jan. 1996, pp. 1-9.
Lorenz et al., "In vivo blockade of TNF-alpha by intravenous infusion of a chimeric monoclonal TNF-alpha antibody in patients with rheumatoid arthritis. Short term cellular and molecular effects", The Journal of Immunology, vol. 156, No. 4, 1996, pp. 1646-1653.
Ma et al., "Using precipitation by polyamines as an alternative to chromatographic separation in antibody purification processes", Journal of Chromatography B, vol. 878, No. 9-10, Mar. 15, 2010, pp. 798-806.
Maharjan et al., "Novel chromatographic separation—The potential of smart polymers", Innovative Food Science and Emerging Technologies, 2007, pp. 1-11.
Stocker Majd, Gisela, "The Affinity Precipitation for the Isolation of Biomolecules", Thèse EPFL, No. 3862, Aug. 2007, 146 pages.
Malmstadt et al., "A Smart Microfluidic Affinity Chromatography Matrix Composed of Poly(N-isopropylacrylamide)-Coated Beads", Analytical Chemistry, vol. 75, No. 13, Jul. 1, 2003, pp. 2943-2949.
Malmstadt et al., "Affinity Thermoprecipitation and Recovery of Biotinylated Biomolecules via a Mutual Streptavidin-Smart Polymer Conjugate", Bioconjugate Chem., vol. 14, No. 3, 2003, pp. 575-580.

Marks et al., "By-passing immunization : Human antibodies from V-gene libraries displayed on phage", Journal of Molecular Biology, vol. 222, No. 3, Dec. 5. 1991, pp. 581-597.
Marks et al., "By-Passing Immunization: Building High Affinity Human Antibodies by Chain Shuffling", Nature Biotechnology, vol. 10, 1992, pp. 779-783.
McCafferty et al., "Phage antibodies: filamentous phage displaying antibody variable domains", Nature, vol. 348, Dec. 6, 1990, pp. 552-554.
Millstein et al., "Hybrid hybridomas and their use in immunohistochemistry", Nature, vol. 305, Oct. 6, 1983, pp. 537-540.
Morimoto et al., "Single-step purification of F(ab').sub.2 fragments of mouse monoclonal antibodies (immunoglobulins G1) by hydrophobic interaction high performance liquid chromatography using TSKgel Phenyl-5PW", Journal of Biochemical and Biophysical Methods, vol. 24, 1992, pp. 107-117.
Morrison et al., "Chimeric human antibody molecules: Mouse antigen-binding domains with human constant region domains", Proc. Nati. Acad. Sci. USA, vol. 81, Nov. 1984, pp. 6851-6855.
International Search Report received for PCT Application No. PCT/US2007/026040, mailed on Mar. 31, 2008, 1 page.
International Search Report received for PCT Application No. PCT/US2007/026090, mailed on Apr. 24, 2008, 1 page.
International Search Report received for PCT Application No. PCT/US2008/013736, mailed on Aug. 27, 2009, 5 pages.
International Search Report received for PCT Application No. PCT/US2009/006363, mailed on Feb. 18, 2010, 3 pages.
Peram et al., "Monoclonal antibody purification using cationic polyelectrolytes: An alternative to column chromatography", Biotechnology Progress, vol. 26, No. 5, Sep./Oct. 2010, pp. 1322-1331.
Persson et al., "Flocculation of Cell Debris for Improved Separation Centrifugation", Flocculation in Biotechnology and Separation Systems, 1987, pp. 457-466.
Presta et al., "Humanization of an antibody directed against IgE", The Journal of Immunology, vol. 151, No. 5, 1993, pp. 2623-2632.
Presta, Leonard G., "Antibody engineering", Current Opinion in Structural Biology, vol. 2, No. 4, Aug. 1992, pp. 593-596.
Richman et al., Radioimmunotherapy for Breast Cancer Using Escalating Fractionated Doses of 131I-labeled Chimeric L6 Antibody with Peripheral Blood Progenitor Cell Transfusions—, Cancer Research (Suppl.), vol. 55, Dec. 1, 1995, pp. 5916s-5920s.
Riechmann et al., "Reshaping human antibodies for therapy", Nature, vol. 332, Mar. 24, 1988, pp. 323-327.
Riske et al., "The use of chitosan as a flocculant in mammalian cell culture dramatically improves clarification throughput without adversely impacting monoclonal antibody recovery", Journal of Biotechnology, vol. 128, No. 4, Mar. 10, 2007, pp. 813-823.
Seo et al., "Structure and Hydrolysis Activity of Poly(allylamine)s having Hydrophobic Groups", Journal of the Chemical Society of Japan, No. 8, Aug. 1991, pp. 1115-1126. (English Abstract Submitted).
Roush et al., "Advances in Primary Recovery: Centrifugation and Membrane Technology", Biotechnology Progress, vol. 24, No. 3, May/Jun. 2008, pp. 488-495.
Saitoh et al., "Concentration of Hydrophobic Organic Compounds by Polymer-Mediated Extraction", Anal. Chem., vol. 71, No. 20, 1999, pp. 4506-4512.
Sakohara et al., "Flocculation Mechanism of Suspended Particles Using the Hydrophilic/Hydrophobic Transition of a Thermosensitive Polymer", Kona, No. 20, 2002, pp. 246-250.
Schmaljohann, Dirk, "Thermo- and pH-responsive polymers in drug delivery", Advanced drug delivery reviews, vol. 58, No. 15, 2006, pp. 1655-1670.
Schwarz et al., "Cationic Flocculants Carrying Hydrophobic Functionalities: Applications for Solid/Liquid Separation", The Journal of Physical Chemistry B, vol. 111, No. 29, 2007, pp. 8649-8654.
Senstad et al., "Purification of Wheat Germ Agglutinin Using Affinity Flocculation with Chitosan and a Subsequent Centrifugation or Flotation Step", Biotechnology and Bioengineering, vol. 34, Jan. 1, 1989, pp. 387-393.

(56) References Cited

OTHER PUBLICATIONS

Shalaby et al., "Development of humanized bispecific antibodies reactive with cytotoxic lymphocytes and tumor cells overexpressing the HER2 protooncogene", J. Exp. Med., vol. 175, Jan. 1, 1992, pp. 217-225.

Shan et al., "Flocculation of cell, cell debris and soluble protein with methacryloyloxyethyl trimethylammonium chloride—acrylonitrile copolymer", Journal of Biotechnology, vol. 49, 1996, pp. 173-178.

Sharkey et al., "Evaluation of a complementarity-determining region-grafted (humanized) anti-carcinoembryonic antigen monoclonal antibody in preclinical and clinical studies", Cancer Research (Suppl.),, vol. 55, 1995, pp. 5935s-5945s.

Sims et al., "A humanized CD18 antibody can block function without cell destruction", The Journal of Immunology, vol. 151, No. 4, 1993, pp. 2296-2308.

St. John et al., "Immunologic therapy for ARDS, septic shock, and multiple-organ failure", Chest, vol. 103, 1993, pp. 932-943.

Stamenkovic et al., "The B lymphocyte adhesion molecule CD22 interacts with leukocyte common antigen CD45RO on T cells and α2-6 sialyltransferase, CD75, on B cells", Cell, vol. 66, No. 6, Sep. 20, 1991, pp. 1133-1144.

Stoppa et al., "Anti-LFA1 monoclonal antibody (25.3) for treatment of steroid-resistant grade III-IV acute graft-versus-host disease", Transplant International, vol. 4, No. 1, Jan. 1991, pp. 3-7.

Suedee et al., "Temperature sensitive dopamine-imprinted (N,N-methylene-bis-acrylamide cross-linked) polymer and its potential application to the selective extraction of adrenergic drugs from urine", Journal of Chromatography A, vol. 1114, May 12, 2006, pp. 239-249.

Toei, Kyoji "Ion-Association Reagents A Review", Analytical Sciences, vol. 3, No. 6, 1987,pp. 479-488.

Traunecker et al., "Bispecific single chain molecules (Janusins) target cytotoxic lymphocytes on HIV infected cells", The EMBO Journal, vol. 10, No. 12, Jul. 1, 1991, pp. 3655-3659.

Tutt et al., "Trispecific F(ab')3 derivatives that use cooperative signaling via the TCR/CD3 complex and CD2 to activate and redirect resting cytotoxic T cells", The Journal of Immunology, vol. 147, 1991, pp. 60-69.

Unz, Richard F., "Aspects of Bioglocculation: An Overview", Flocculation in Biotechnology and Separation Systems, 1987, pp. 351-368.

Vaughan et al., "Human Antibodies with Sub-nanomolar Affinities Isolated from a Large Non-immunized Phage Display Library", Nature Biotechnology, vol. 14, Mar. 1996, pp. 309-314.

Verhoeyen et al., "Reshaping human antibodies: grafting an antilysozyme activity", Science, vol. 239, Mar. 25, 1988, pp. 1534-1536.

Waterhouse et al., "Combinatorial infection and in vivo recombination: a strategy for making large phage antibody repertoires", Nucleic Acids Research, vol. 21, No. 9, 1993, pp. 2265-2266.

Westoby et al., "Effects of solution environment on mammalian cell fermentation broth properties: Enhanced impurity removal and clarification performance", Biotechnology and Bioengineering, vol. 108, No. 1, Jan. 1, 2011, pp. 50-58.

Wickramasinghe et al., "Clearance of minute virus of mice by flocculation and microfiltration", Biotechnology and Bioengineering, vol. 86, No. 6, Jun. 20, 2004, pp. 612-621.

Wickramasinghe et al., "Enhanced microfiltration of yeast by flocculation", Desalination, vol. 147, No. 1-3, Sep. 10, 2002, pp. 25-30.

Yu et al., "Selective Precipitation of Water-Soluble Proteins Using Designed Polyelectrolyte", Separation Science and Technology, vol. 37, No. 1, 2002, pp. 217-228.

Zapata et al., "Engineering linear F(ab')2 fragments for efficient production in *Escherichia coli* and enhanced antiproliferative activity", Protein Engineering, vol. 8, No. 10, 1995, pp. 1057-1062.

Attia Yosry A., "Flocculation in biotechnology and separation systems", Process Technology Proceedings, 4, Proceedings of the International Symposium on Flocculation in Biotechnology and Separation Systems, vol. 8, No. 10, Jul. 28-Aug. 1, 1986, pp. 429 & 441.

"Merriam Webster Dictionary", available online at <http://www.merriam-webster.com/dictionary/associated>, retrieved on May 15, 2013, 4 pages.

"Ultrafiltration Discs and Stirred Cells" available online at <www.millipore.com/amicon>, Solvent-resistant Stirred Cells, p. 127.

International Preliminary Report on Patentability received for PCT Patent Application No. PCT/US2009/006363, mailed on Jun. 21, 2011, 6 pages.

International Search Report and Written Opinion received for PCT Patent Application No. PCT/US2009/067097, dated Jan. 29, 2010, 7 pages.

International Preliminary Report on Patentability & Written Opinion received for PCT Patent Application No. PCT/US2009/067097, mailed on Jun. 30, 2011, 7 pages.

International Preliminary Report on Patentability received for PCT Patent Application No. PCT/US2011/036648, mailed on Nov. 29, 2012, 9 pages.

International Preliminary Report on Patentability received for PCT Patent Application No. PCT/US2011/039595, mailed on Dec. 20, 2012, 10 pages.

International Search Report and Written Opinion received for PCT Application No. PCT/US2011/039595 mailed on Dec. 6, 2011, 15 pages.

Fujii et al., "Application of Reversibly soluble polymers in Bioprocessing", Trends in Biotechnology, vol. 9, 1991, pp. 191-196.

Galaev et al., "'Smart' Polymers and What They Could Do in Biotechnology and Medicine", Trends in Biotechnology, vol. 17, No. 8, Aug. 1999, pp. 335-340.

International Search Report and Written Opinion received for PCT Application No. PCT/US2011/036648, mailed on Oct. 31, 2011, 5 pages.

Seo et al., "Self-organization of Poly(allylamine)s Containing Hydrophobic Groups and Its Effect on the Interaction With Small Molecules. 1. Static Fluorometry", Macromolecules, vol. 24, No. 15, 1991, pp. 4255-4263.

Agarwal et al., "Sequential Precipitation with Reversibly Soluble Insoluble Polymers as a Bioseparation Strategy: Purification of β-Glucosidase from *Trichoderma longibrachiatum*", Protein Expression and Purification, vol. 7, 1996, pp. 294-298.

Galaev et al., "Interaction of Cibacron Blue with Polymers: Implications for Polymer-Shielded Dye-Affinity Chromatography of Phosphofructokinase from Baker's Yeast", Journal of Chromatography A, vol. 684, 1994, pp. 45-54.

Lali et al., "Carboxymethyl Cellulose as a New Heterobifunctional Ligand Carrier for Affinity Precipitation of Proteins", Bioseparation, vol. 7, 1999, pp. 195-205.

\* cited by examiner

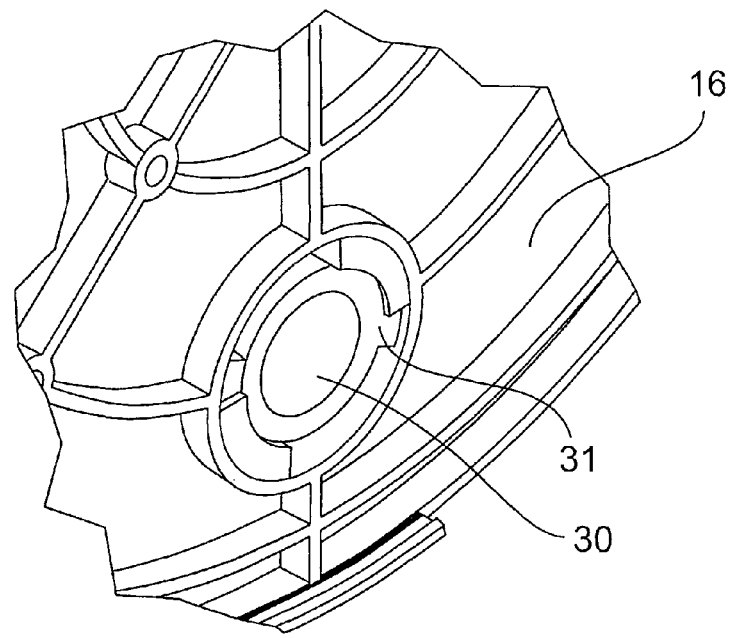
Figure 7a
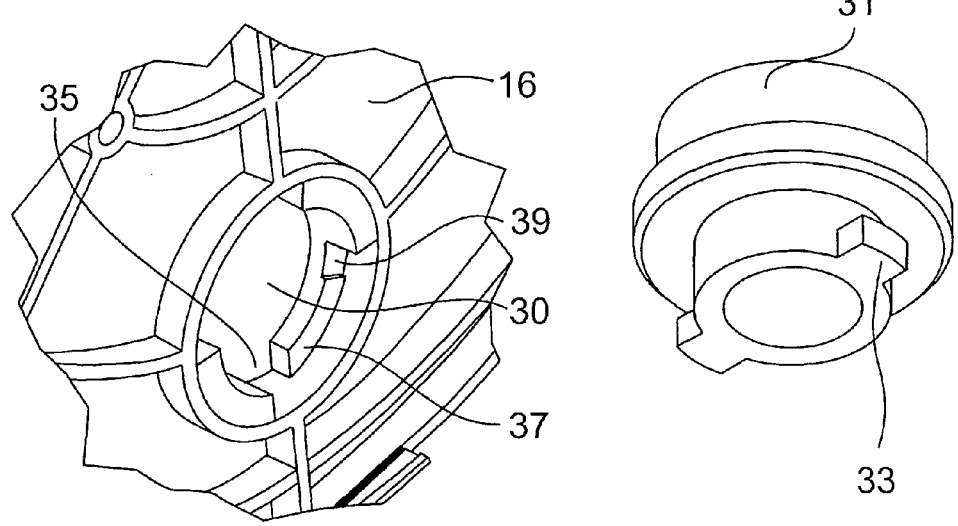 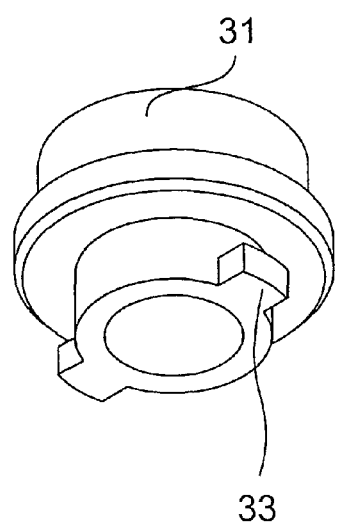
Figure 7b    Figure 7c

STIRRED TANK BIOREACTOR

CROSS-REFERENCED TO RELATED APPLICATIONS

This application claims the benefit of U.S. Provisional Patent Application No. 61/131,640, filed on Jun. 11, 2008, the entire contents of which are incorporated by reference herein.

The present invention relates to a disposable stirred tank bioreactor. More particularly, it relates to a stirred tank reactor formed of a molded plastic having one or more ports molded therein.

BACKGROUND OF THE INVENTION

Many small scale bioreactors of the size from about 1 liter to about 200 liters are formed of glass or steel, preferably stainless steel. Typical volumes for bench top versions are 2-10 liters. All have a solid body and a removable top sealed to the body by an o-ring. The top contains ports for probes, sampling, air sparging, media exchange, and a stir rod for circulation. They are typically used for culturing or fermenting various organisms such as plants, bacteria (e.g. *E. coli*), animal cells (e.g. Chinese Hamster Ovary (CHO) cells), yeast, mold, etc.

After each use (typically 3-15 days), the reactor and its components must be disassembled, cleaned, reassembled, reconfigured and autoclaved before reuse. This is a time consuming, laborious process requiring the disassembly and moving of many heavy and/or small and fragile components. Additionally, one generally needs to validate the cleaning procedure to ensure that it is done correctly time after time with the same consistent results. At best after all the work has been completed, one has rendered the reactor and its components aseptically clean meaning that contamination can still occur by residual organisms or advantageous ones that enter through the aseptic assembly.

Many designs have attempted to overcome these issues by using disposable liners in the glass or stainless tank.

U.S. Pat. No. 6,245,555 suggests using a plastic liner that is inserted within the existing tank to reduce the amount of cleaning and increase the level of asepticness. However, it too has many limitations.

The liner must conform to the inner surface of the tank in order to prevent any discontinuity in the circulation within the device or to prevent the formation of dead spots or pockets in which material may get trapped and fester or create uneven flow throughout the system. However wrinkles in the liner still occur and create the above mentioned problems. All ports are top mounted, limiting the available area for the different components used in the bioreactor (feed lines, airlines, stirrer shafts, motors and journals, sampling ports, probe ports and the like). Additionally, the top plate is releaseably sealed to the liner making only an aseptic connection. Often times the liner system is limited to an air sparging system for both gas transfer and circulation. The use of impeller shafts has been avoided due to the concern that the shaft or impellers may tear the liner during shipping, storage or assembly. Additionally, all probes and samplers enter through the lid or top and have a tube that extends down into the liquid to the desired level. This means that there is often a long dead leg of material that needs to be flushed or removed before and after sampling to ensure that an accurate sample has been obtained. Lastly, lipids and cholesterols are well-known to bind to many of the plastics used for such liners.

What is desired is a disposable tank liner that overcomes the deficiencies with the current state of the art. The present invention provides such a device.

SUMMARY OF THE INVENTION

The present invention is a disposable bioreactor formed of molded plastic so that it can be rigid or at least semi-rigid and can be held in a stand or be self standing. The bioreactor is presterilized and has a top and body sealed to each other. One or more ports are formed in the top and side of the housing. Preferably at least one port is below the liquid/air level for the housing. The one or more ports that are below the liquid/air interface level may be used as sampling ports or access ports for probes. Using such a port allows one to take samples without the need of the dip tube of the prior art eliminating the dead leg and risk of an improper sample or contaminated sample. Additionally, the probe does not need to be long in order to fit down to the desired level in the container. It may simply extend sideways into the liquid at the desired level. Ports below the liquid level are an ideal location for the addition of disposable, optical sensors and provide a means for attaching sensing equipment.

The invention provides a direct retrofit for the existing glass or steel assembly that utilizes the existing support structures, probes for measuring different parameters such as temperature and pH and controls. The molded design overcomes issues of discontinuity, dead spots and the like due to its fixed dimensions that are built in by the molding process. Reproducible probe and other equipment location is also guaranteed through the use of the molded port features. Moreover, the rigid bowl is that it can accept the heating blanket that is used on the glass meaning that there is no need for an external support or heating jacket. The molded plastic allows for greater flexibility in material selection to reduce or eliminate lipid or cholesterol binding. Preferably the system allows for either an air sparging gas/circulation system and/or air sparging for gas transfer and a stirrer/impeller for circulation without fear of damage to the container. Molded containers are self supportive and do not require a support housing as does the flexible liner designs. Additionally with a molded plastic design heating or cooling blankets can be directly attached to the molded body whereas in a flexible bag the blanket must be installed either within or outside of the support housing. Lastly by having one or more ports formed below the liquid/air level one can have a drain that allows for the simple and near complete removal of all liquid when desired.

It is an object of the present invention to provide a bioreactor for culturing or processing a biomass formed of a presterilized, disposable housing made of a plastic selected from the group consisting of semi-rigid and rigid plastic, said housing having a top and a body integrally sealed to each other, the body having an interior space, one or more ports formed in the top and the body respectively of the housing and in fluid communication with the interior of the housing, the one or more ports having a cap to isolate the interior space of the body from the environment.

It is another object of the present invention to provide a bioreactor having two or more ports and at least one port is molded into the body at a level below a liquid/air interface of the housing.

It is a further object of the present invention to provide a bioreactor having the one or more ports are molded into the top and body.

It is an additional object of the present invention to provide a bioreactor further comprising a stirrer shaft with one or more paddles mounted within the body of the housing.

It is another object of the present invention to provide a bioreactor in which the body includes a port adjacent to a portion of the body farthest from the top and the port farthest from the top includes an air diffuser selectively retained to the interior of the body, the diffuser being formed of a frit selected from the group consisting plastic, ceramic and metal frits and the port being connected to a gas line on the exterior portion of the body.

It is a further object of the present invention to provide a bioreactor having one or more ports wherein the one or more ports of the body are connected to Luer fittings.

It is an object to provide a bioreactor having a stirrer shaft with one or more paddles mounted within the body of the housing and a retainment hub located at the bottom of the body of the bioreactor to retain and center the shaft.

These as well as other advantages which will become apparent form the disclosure below.

IN THE DRAWINGS

Figure 4A:
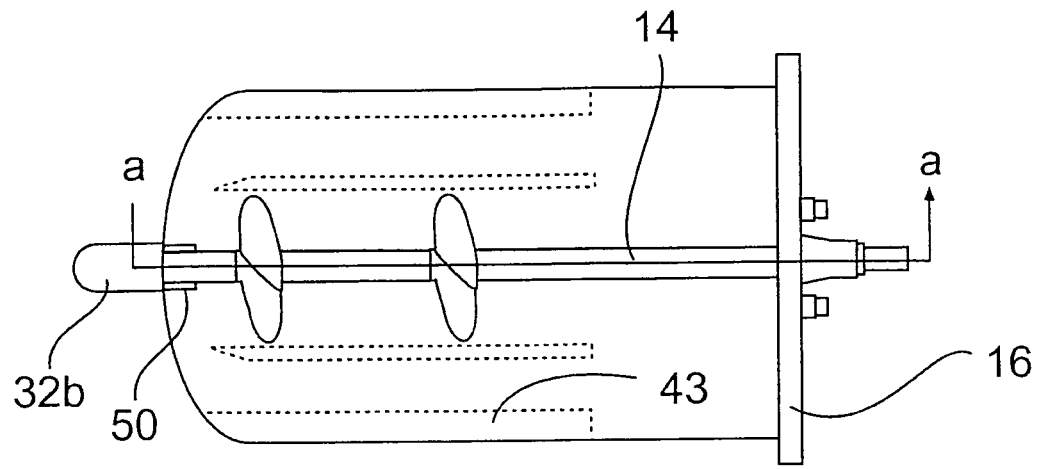
Figure 4B:
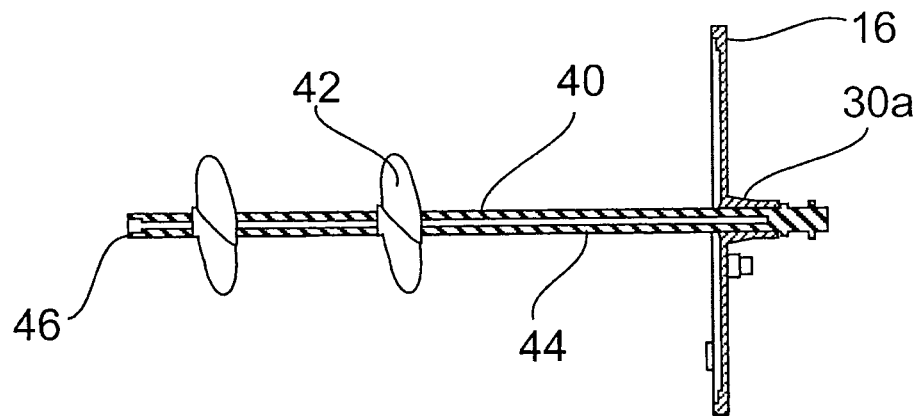
Figure 4C:
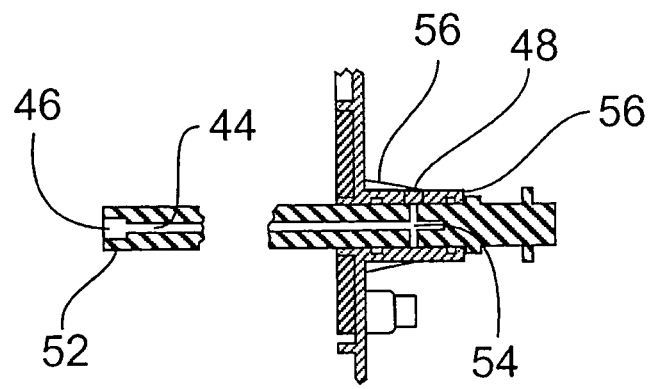

FIGS. 4A-C show alternative stirring mechanisms of the present invention in cross-sectional view.

Figure 5:
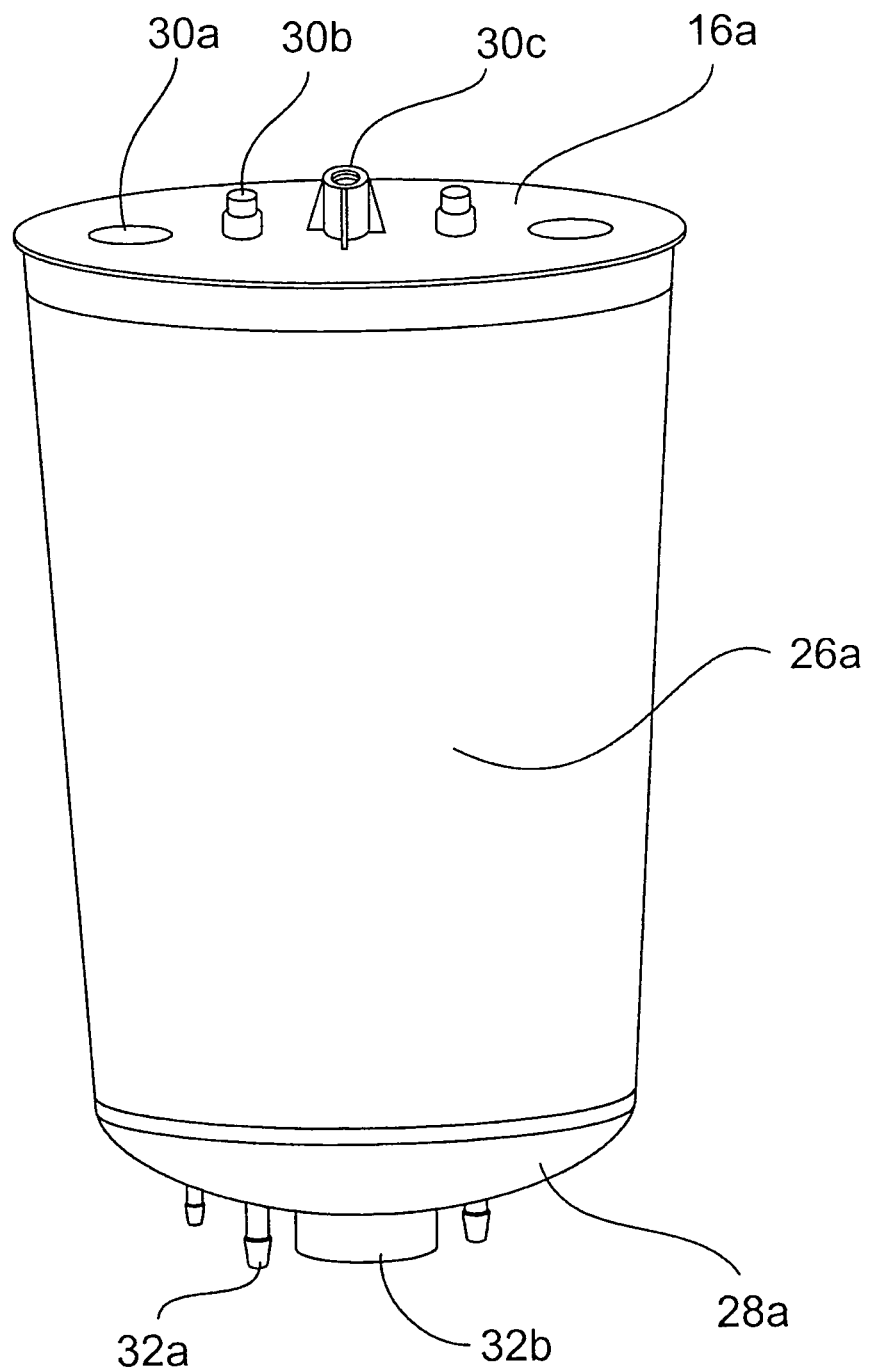

FIG. 5 shows an alternative embodiment of the body of the present invention in perspective view.

Figure 6:
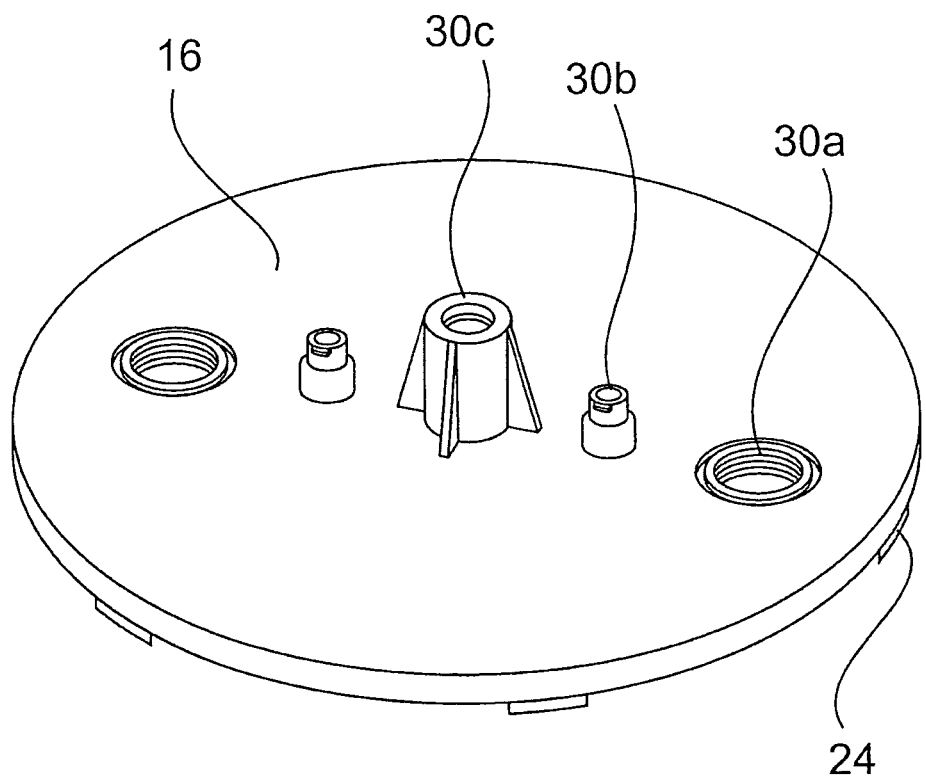

FIG. 6 shows one embodiment of the top according to the present invention in perspective view.

FIGS. 7A-C show one type of fitting and its manner of attachment to one type of port of the present invention in perspective view.

Figure 8:
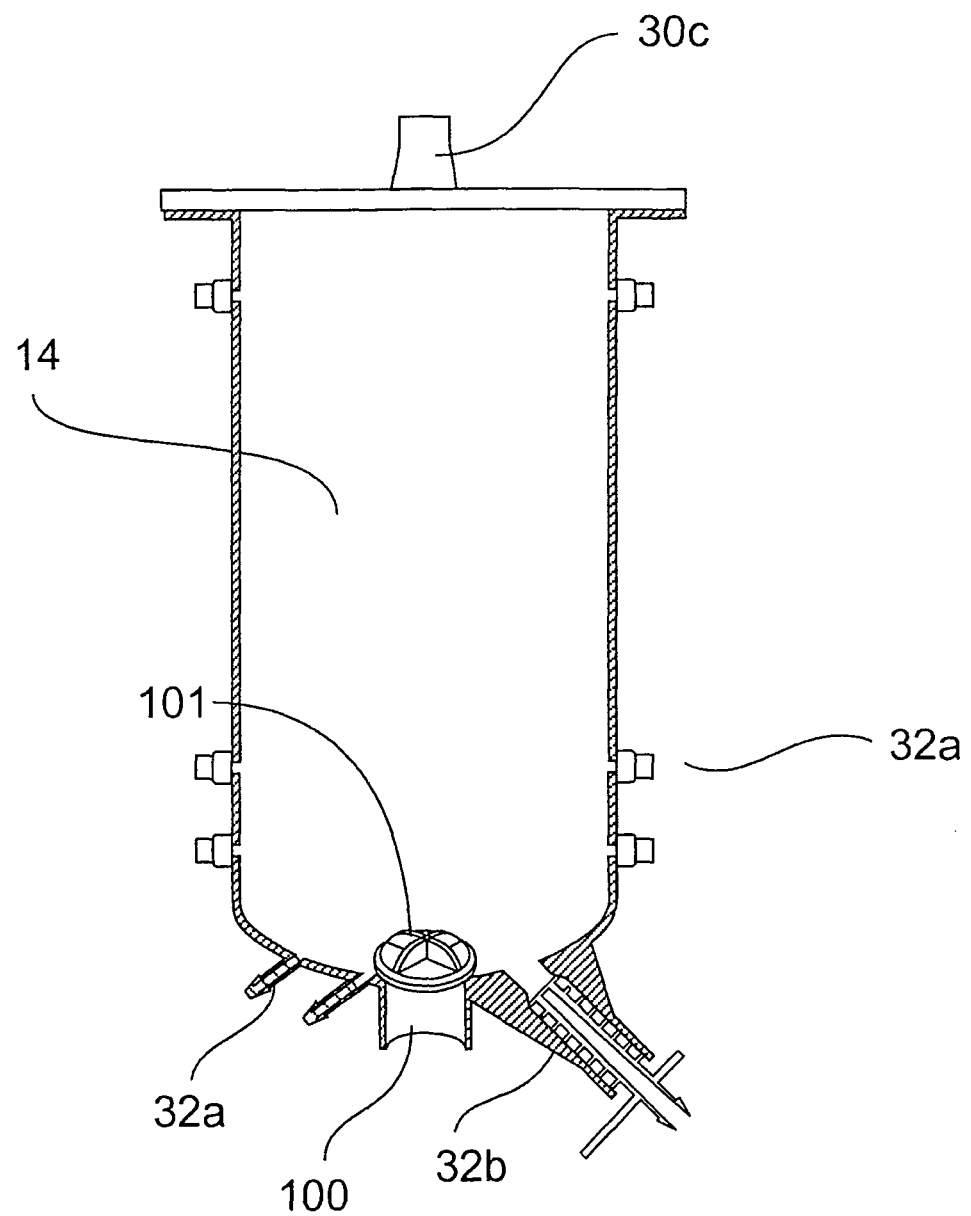

FIG. 8 shows an alternative embodiment of the present invention.

Figure 9:
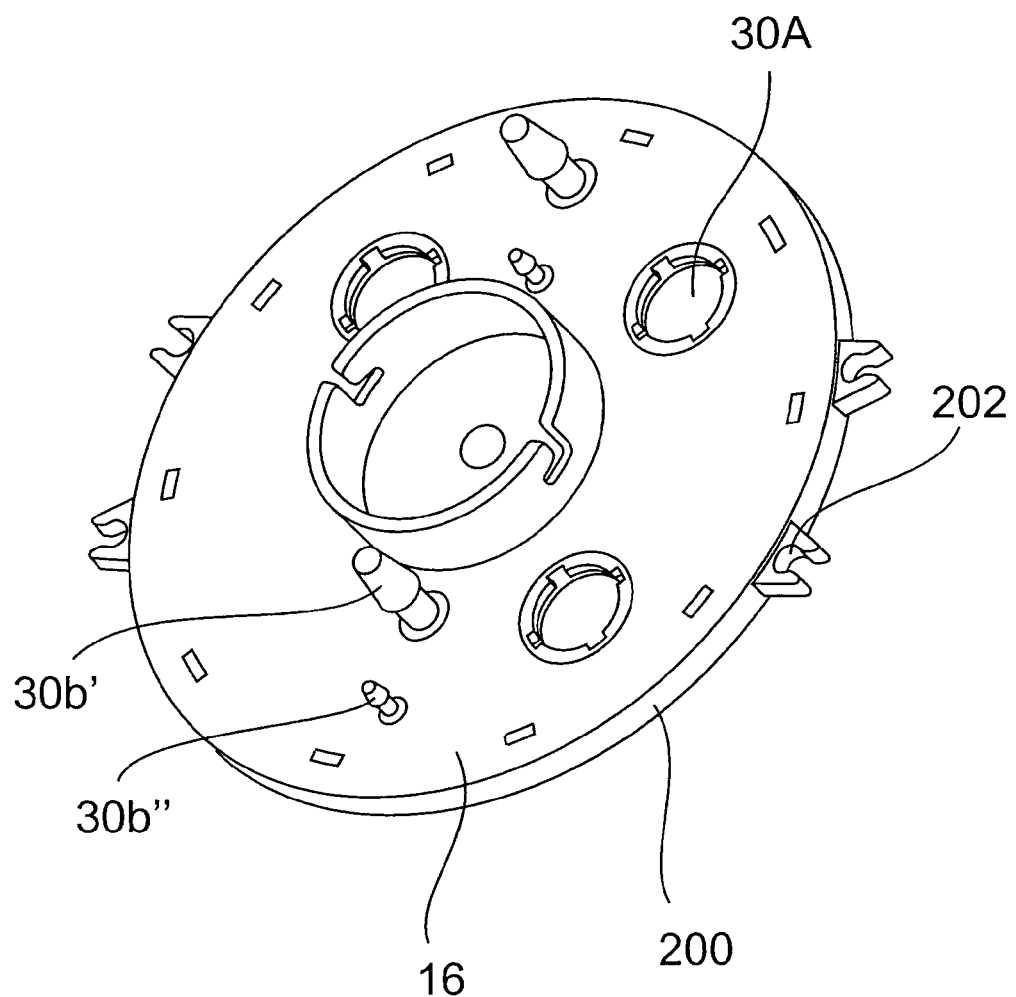

FIG. 9 shows one embodiment of the top according to the present invention in perspective view.

Figure 10:
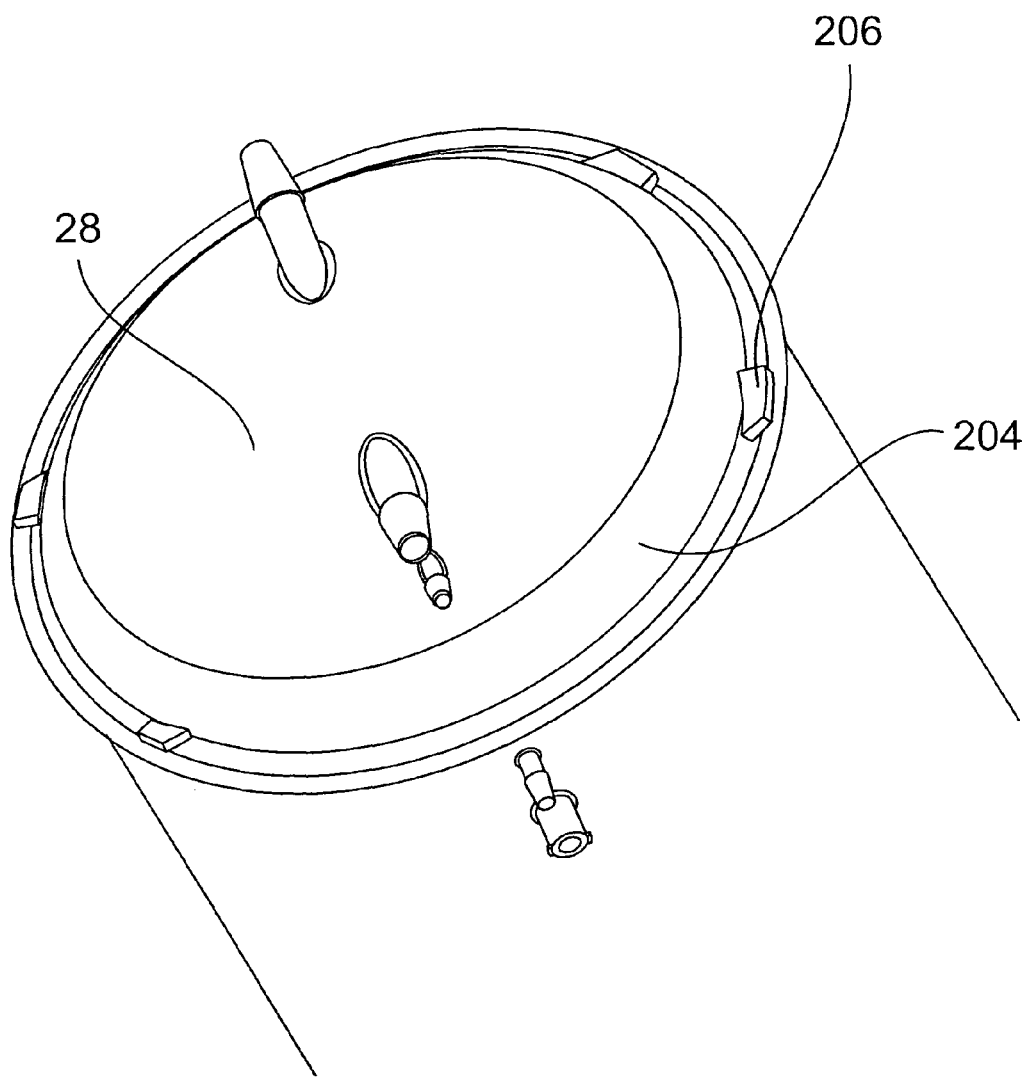

FIG. 10 shows one embodiment of the bottom of the bioreactor according to the present invention in perspective view.

Figure 11:
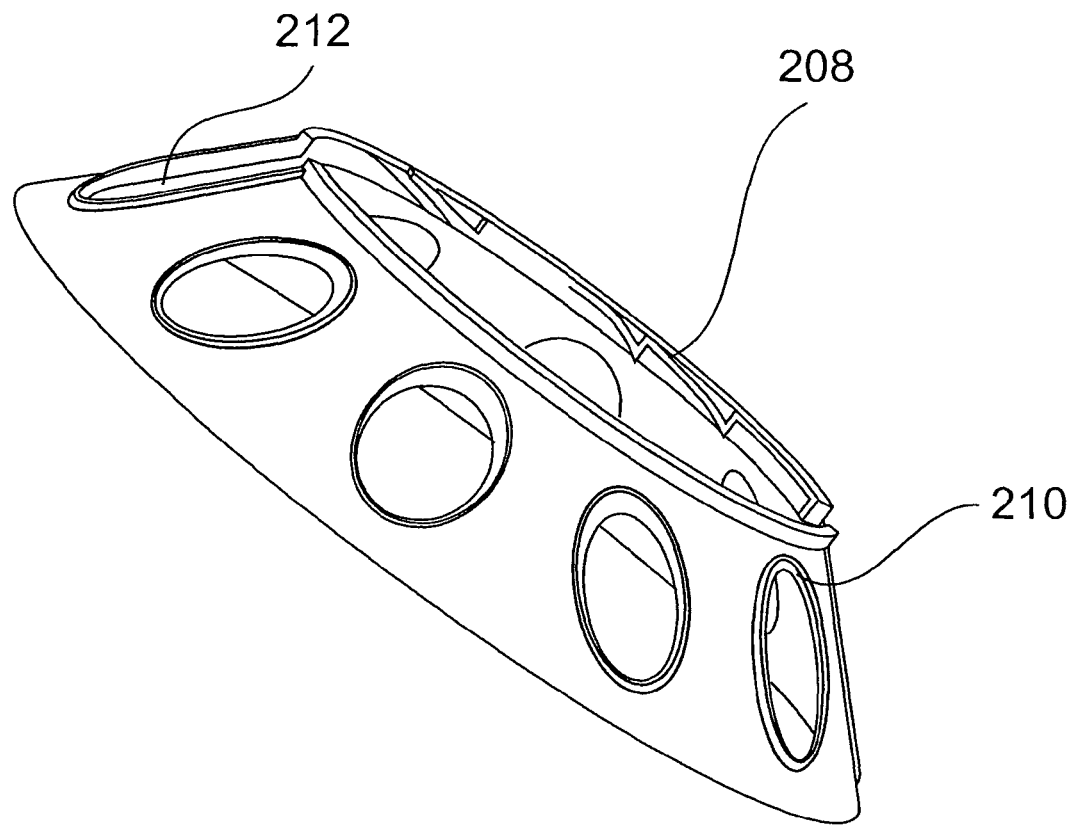

FIG. 11 shows one embodiment of a different support that interfaces with the bottom of the bioreactor shown in FIG. 10 according to the present invention in perspective view.

Figure 12:
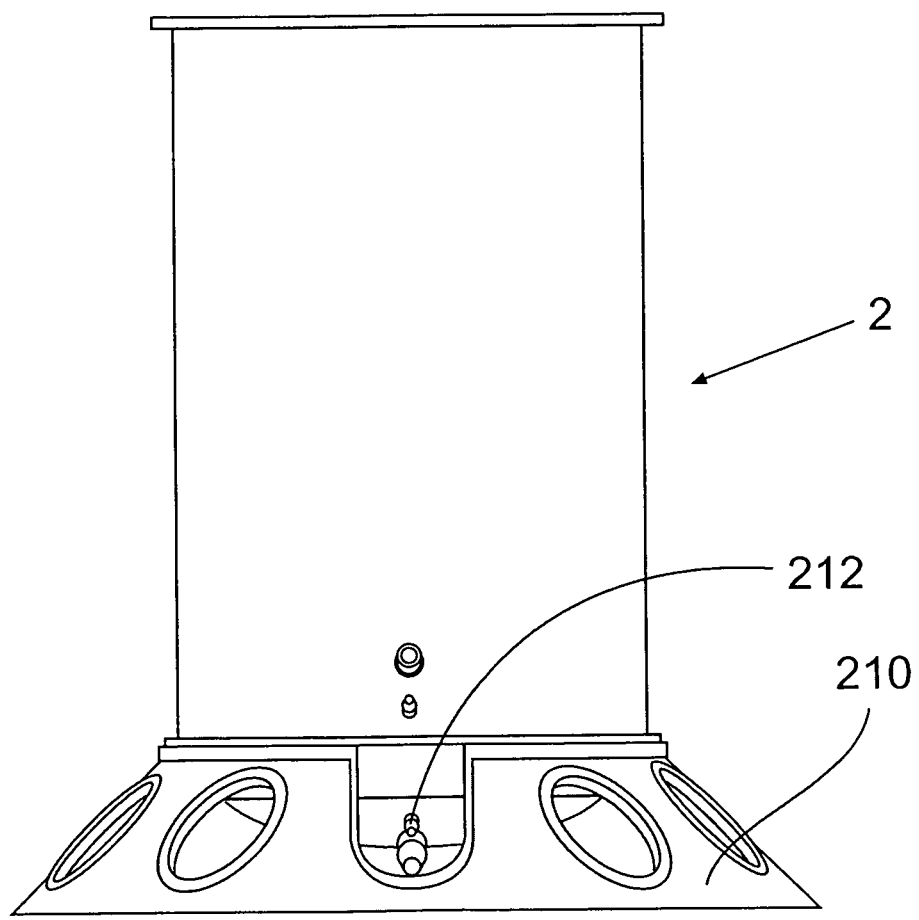

FIG. 12 shows the bioreactor of FIG. 10 connected to the base of FIG. 11 in perspective view.

DETAILED DESCRIPTION OF THE INVENTION

Figure 1:
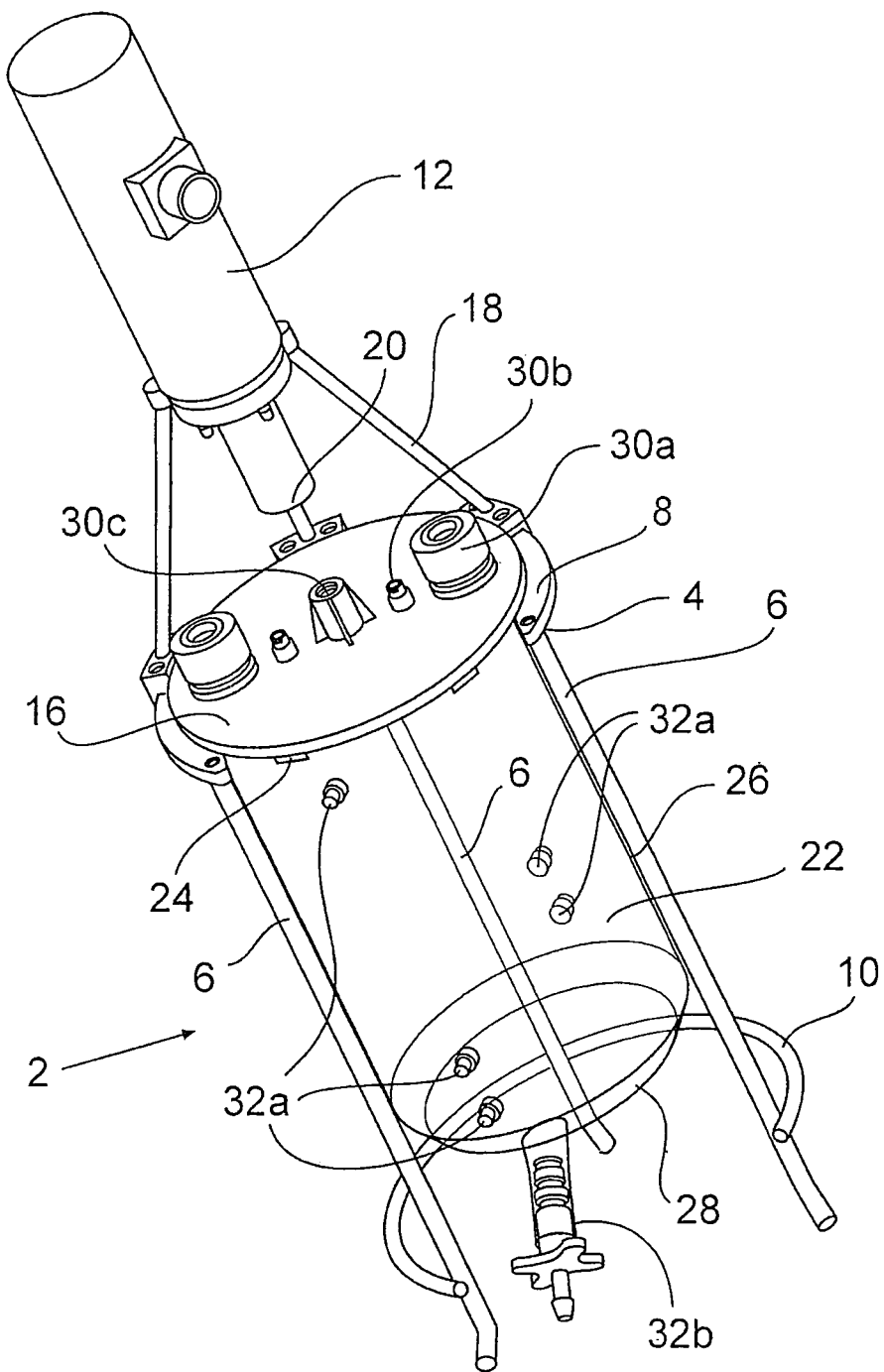
FIG. 1 shows a first embodiment of the present invention in perspective view.

FIG. 1 shows an embodiment of the present invention. The bioreactor 2 is held in a stand 4 which is comprised of several legs 6 (in this embodiment 3 legs although one continuous leg or 2 large legs or more than 3 legs can also be used) and a support rim 8. As shown the legs 6 may have an optional support piece 10 at or near the bottom to keep the legs 6 from spreading when the bioreactor 2 is filled and in the stand 4.

Depending upon the type of circulation system used the stand 4 may also support the drive mechanism 12 (as shown) for the circulation mechanism, which typically is a stirrer or paddle assembly 14 as will be described in greater detail later. In this particular embodiment, the drive mechanism 12 is a motor and is mounted to the top of the centered above the top 16 of the bioreactor 2 by several arms 18 (although 3 are shown alternative numbers may be used). Other features such as mounting blocks (not shown) and the like may be formed on the top 16 or support rim 8 to support the drive mechanism 12. As shown the drive mechanism 12 has a shaft 20 that can be attached to the stirrer as explained later herein. Other stands can be used in lieu of the design described above and will work equally well.

The bioreactor body 22 has an interior space into which the fluids, cells, probes and other devices of the bioreactor are at least partially contained. The body 22 is sealably attached to the top 16. This may be by a mechanical seal such as a rubber gasket and clips 24 (as shown) or by a clamp, such as a band clamp or Ladish or TriClover clamp, mated threads on the top 16 and body 22 and the like. Alternatively, they may be sealed by adhesives or heat sealing of the top 16 to the body 22 or formed together in one piece such as in a rotomolding apparatus.

The body 22 has one or more sidewalls 26 that extend downwardly from the top 16 and terminate in a closed bottom 28, preferably having a hemispherical shape. As shown, there is one sidewall 26 of a circular design which is a retrofit for existing glass and metal bodies. Alternatively, there can be 3, 4, or more sidewalls if desired (not shown).

Preferably, the body is made of a single piece of molded plastic. Alternatively it may be made of two or more pieces of plastic that are sealed together such as by heat, glue, or gaskets (not shown).

In another alternative arrangement shown in FIG. 5, only the top 16a and bottom 28a are made of molded plastic and the one side wall 26a in this embodiment is formed of flexible plastic such as a plastic film. This still allows for the use of one or more ports in the device below the liquid/air level. Also notice that the port(s) such as 32a may terminate in a hose barb or other connective feature if desired.

Also formed in the bioreactor 2 of this embodiment are one or more ports 30 (in this embodiment there are three types 30a-c (for a total of 5 ports) formed in the top 16 and one or more ports 32 in the body 22 (in this embodiment there are at least two different types 32a-b for a total of seven ports overall in this embodiment). The top 16 and body 22 may have multiple ports of similar and/or of different styles to provide one with the number of ports, of the desired type, in the desired locations throughout the bioreactor 2. These ports 30, 32 or at least a portion of them are formed as part of the top 16 and/or body 22. They may be formed with threads that mate to sealable covers such as closed caps, gasketed caps with a throughbore within the gasket, or various Luer fittings. Alternatively, one or more of the ports can be made in the plastic top 16 and/or body 22 by drilling or burning a hole and then mounting (such as by heat bonding or adhesives) a port in place through or around the hole. Many different port styles and sizes can be accommodated in this invention.

Figure 2:
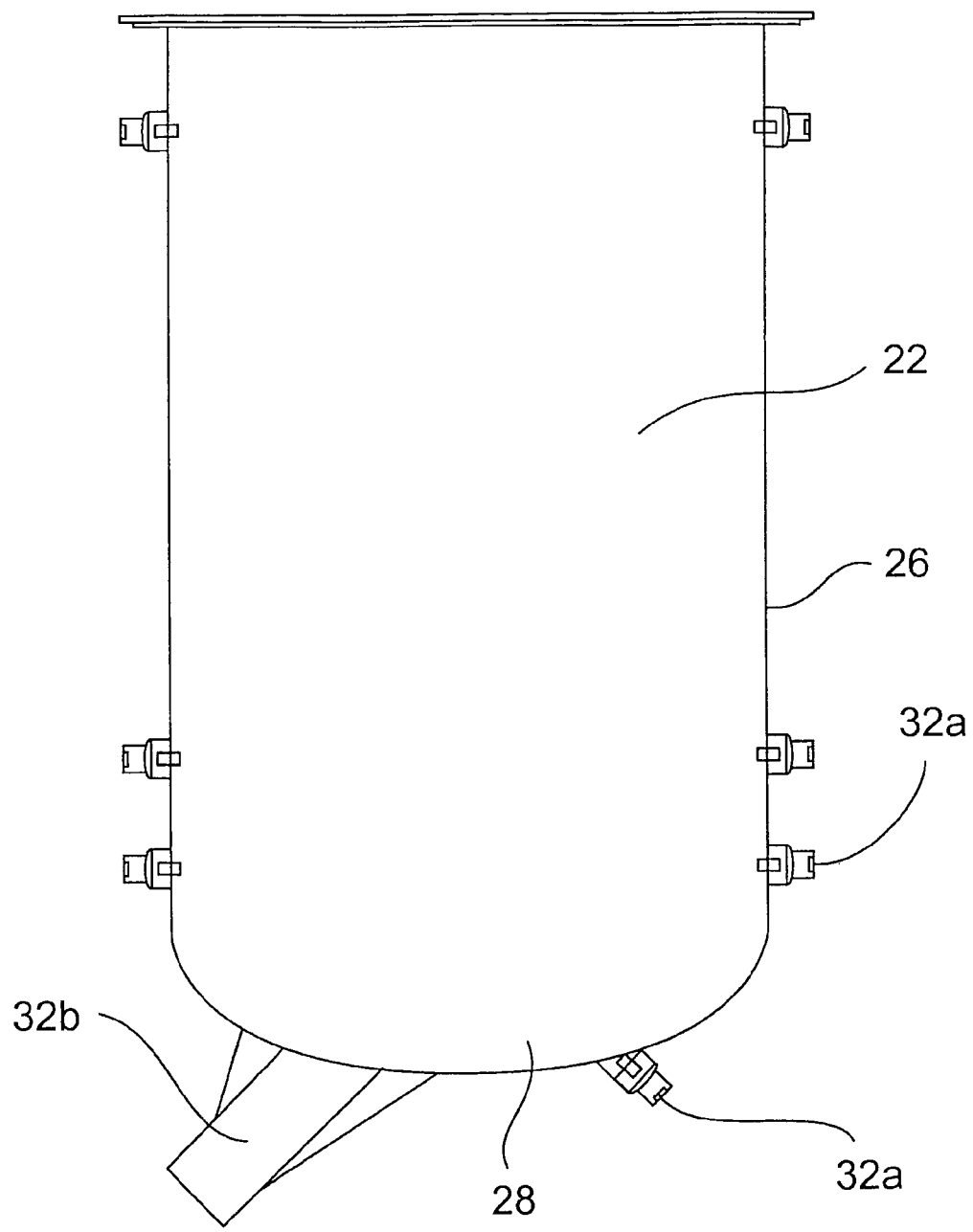
FIG. 2 shows a first embodiment of the body of the present invention in cross-sectional view.

Ports 30a may be used for liquid or gas entrance or exit or for probes such as pH probes, thermometers or thermocouples or the like. Ports 30b may be used for similar purposes. Port 30c is for the stirrer shaft described in further detail herein. Alternatively, if the bioreactor is an airlift design and doesn't use a stirrer rod, the port 30c may be used to house the airline to the sparger at or near the bottom of the body or for any other desired purpose. Ports 32a may be used for sampling of the liquid or for probes such as pH, temperature, dissolved oxygen, lactose level, etc as are common on such bioreactors. Ports 32a while shown as being formed on the sidewall 26 may also be formed in the bottom if desired as shown in FIG. 2. Port 32b is valved port which can be used to supply gas to the body 22 and/or as a drain or outlet from the body. It may serve both functions by attaching a 3 position valve or Y-shaped tube with valves such as pinch valves on each arm of the Y to control flow (not shown). One suitable system for the valve of port 32b is a LYNX® connector available from Millipore Corporation of Billerica, Mass. and as shown in US2005/0016620.

Preferably, one or more ports 32 of the body are formed in a location that is below the normal liquid/gas interface level of the bioreactor.

If desired, one or more of the ports 32a or b in FIGS. 1 and/or 2 may be used to provide gases to the body's interior. A plastic frit such as a POREX® microporous membrane or ceramic stone or sintered metal filter may be attached to the inside of the port within the body to provide the sized gas bubbles desired. Alternatively, a port 30a in the top 16 may be used to hold a tube that extends down into the body to provide the gas supply. Again it may use a frit or ceramic stone or sintered metal filter to provide the desired bubble size.

Figure 3:
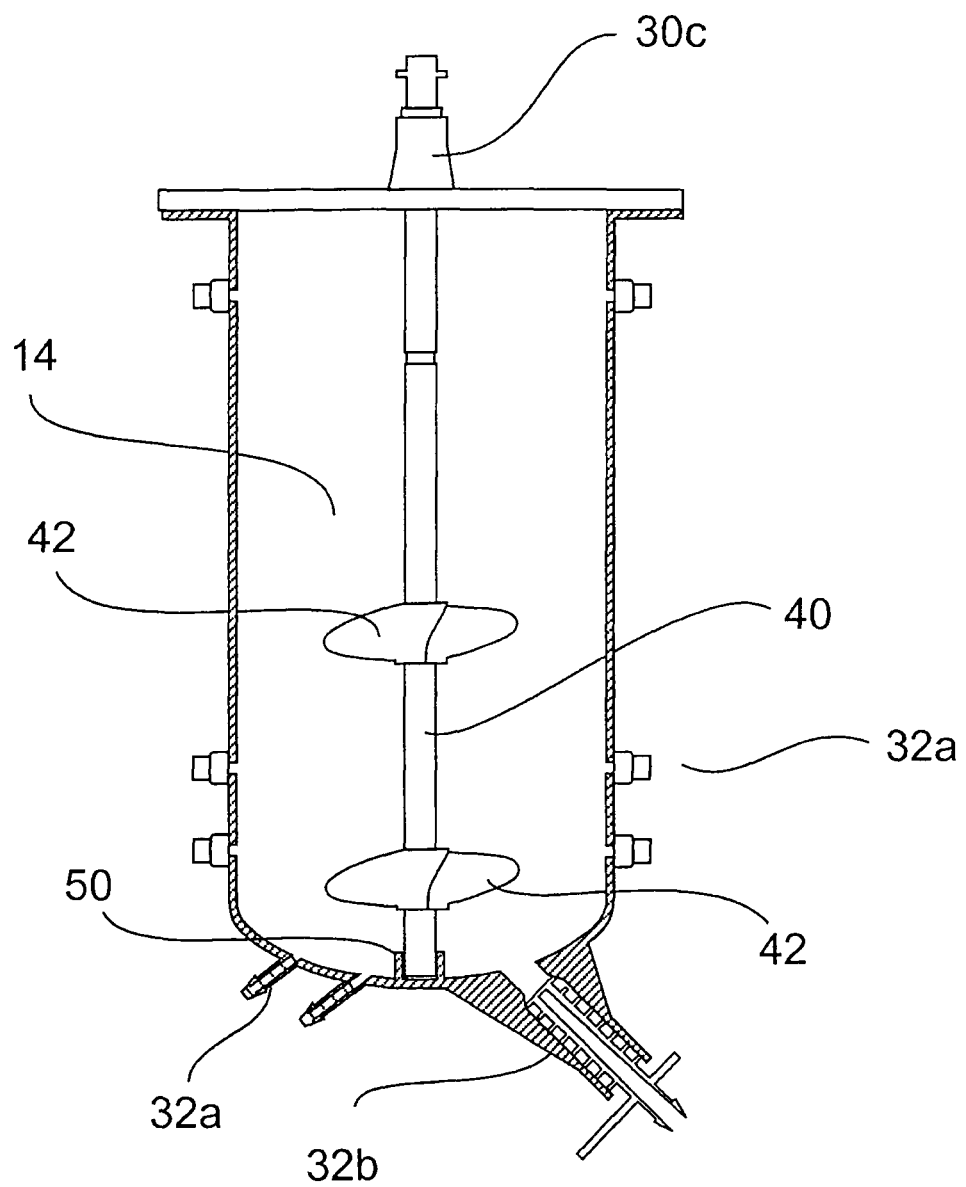
FIG. 3 shows a first embodiment of the present invention in cross-sectional view.

FIG. 3 shows a bioreactor 2 with top 16 and body 22 sealed to each other and the stirring mechanism 14 in place. The stirring mechanism is formed of a shaft 40 and one or more paddles 42. The shaft 40 extends through port 30c and is connected to the shaft 20 of the drive mechanism 12 (not shown). Preferably one or more o-rings in the port 30c allow for movement of the shaft 40 without compromising the integrity of the seal within the body 22.

FIG. 4A shows a stirrer 14 and a retainment hub 50 formed in the bottom of the body 22. The retainment hub 50 locates and holds a portion of the shaft so that the shaft does not become dislodged during shipping, storage or use. Also an optional element, vanes 43 is shown in FIG. 4A. These vanes can be molded into the inner surface of the body 22 and extend outward into the interior or they may be separately added after molding. The vanes 43 help to direct flow and ensure that adequate mixing occurs within the bioreactor 2.

FIGS. 4B and C show an alternative design to the stirrer 14. In this embodiment, the gas supply line is built into the stirrer shaft 40. The shaft 40 has a hollow central bore 44 running through at least a portion of the shaft. At or near the bottom of the shaft 40 is a gas outlet 46 which may contain a frit, ceramic stone or sintered metal filter 52 to create the desired bubble size. Gas enters the bore 44 through gas port 48 in port 30a. One or more gas conduits 54 connect the inner portion of the port 30a with the bore 44. One or more, in this instance 2 gaskets 56 such as o-rings are mounted above and/or below the gas port 48 to ensure the gas flows through the port 48 and into the bore 44 through conduit(s) 54 and does not escape to the atmosphere or compromise the integrity of the body. In use the gas flows from a supply into port 48 then into conduit(s) 54 and down the central bore 44 to the gas outlet 46 in the shaft and then into the inner volume of the body 22.

FIG. 6 show one embodiment of the top 16 with some of the various port configurations and styles that are possible with the present invention. For example port 30a may be a screw thread style of port into which a gas or liquid line or probe with matching mating threads is threaded to create a liquid tight seal.

FIGS. 7A-C show another port/fitting style. The fitting 31 as shown in FIG. 7C has cam lock 33. This cam lock mates with a mating cam lock holder 35 in the port 30 (FIG. 7B). The fitting 31 is inserted into port 30 by first aligning the cam locks 33 of the fitting 31 with the cam opening 35 of the port 30. It is then pushed downward and rotated to ride over the cam ramp 37 and terminate and seat itself in the cam lock retainer 39 of the port 30.

FIG. 8 shows an alternative embodiment of the present invention incorporating a magnetic mixer 101 within the body 14 driven remotely from a magnetic drive 100 located on the outer surface of the body 14.

FIG. 9 shows an alternative top 16 of the invention to that shown in FIG. 6 in that at least one or more portions of the top 16 incorporates tube clips 202 which can hold the various tubes of the system in an organized and orderly arrangement. Preferably, the tube clips 202 are formed on an outer edge 200 of the top 16 although if desired some or all of them may also be attached to the upper surface of the top (not shown). In this illustrated embodiment, four clips 202 are shown although more or less may be used if desired. Preferably they are molded as part of the top 16. Alternatively, they may be separately attached by melt bonding, solvent bonding or glues, if desired. Likewise, some or all of the ports, 30b' and 30b", can be in the form of hose barbs as shown rather than screw ports 30 or Luer type fittings as shown in FIG. 6, cam locks of FIG. 7 or other types of fittings discussed below and commonly used by one of ordinary skill in the art. Tubes attached to a hose barb fitting such as 30b' can have tie wraps, connectors such as those taught by US2008/0284163A1 or other devices or can be adhered to the hose barb to keep the tubes in place even when under any pressure that may occur in the system.

FIG. 10 shows an alternative bottom portion 28 of the bioreactor 2 to that shown in FIGS. 1-3. In this embodiment, instead of using the stand 6, the bottom outer wall 204 has two or more, preferably three or four, locking tabs 206 either molded as a feature of the bottom outer wall 204 or separately formed and attached to the bottom outer wall 204 such as by heat bonding, solvent bonding or glue.

The locking tabs 206 of the bottom outer wall 204 mate to corresponding locking features 208 of a bottom support 210 shown in FIG. 11. The bioreactor is placed into the support 210 and the locking tabs 206 of the bottom outer wall 204 engage with the locking features 208 of the support 210. This secures the bioreactor 2 to the support 210 so that the bioreactor 2 is held upright in a secure manner as shown in FIG. 12. Additionally, if desired, one or more open slots 212 can be formed in the support 210 so that any tubing or other features that extend out from the bioreactor 2 when the bioreactor and support are mated can be accommodated without removal or pinching. As shown the tabs and features 206, 208 are threaded style devices. However they can be other forms such as cam locks and cam lock holders as used in some of the port embodiments discussed above. The locking feature allows the end user to remove the base from bowl and recycle easily since the base is not in contact with the culture medium and thus does not need to be sterilized.

Fittings such as compression fittings and tube weld, hose barb and pipe threads, when molded directly into the body, reduce holdup volume and simplify the system. Such components are well known and the covers, connectors, septums for sampling (also called piercable needle ports), check or other valves and the like, whether Luer type or not; Luer Lok® fittings; and the like are readily available for mating with these ports from a variety of companies such as Value Plastics, Inc of Fort Collins, Colo.

Suitable polymers which can be used to form the top and body include but are not limited to polycarbonates, polyesters, nylons, PTFE resins and other fluoropolymers, acrylic and methacrylic resins and copolymers, polysulphones, polyethersulphones, polyarylsulphones, polystyrenes, polyetherimides, nylons, polyesters, polyethylene terephthalates (PET), polyvinyl chlorides, chlorinated polyvinyl chlorides, ABS and its alloys and blends, polyolefins, preferably polyethylenes such as linear low density polyethylene, low density polyethylene, high density polyethylene, and ultrahigh molecular weight polyethylene and copolymers thereof, polypropylene and copolymers thereof and metallocene generated polyolefins.

Preferred polymers are polyolefins, in particular polyethylenes and their copolymers; polystyrenes; and polycarbonates.

The top and body may be made of the same polymer or different polymers as desired.

Likewise, the polymers may be clear or rendered optically opaque or light impermeable. When using opaque or light impermeable polymers, it is preferred that their use be limited to the side walls so that one may use optical scanners or readers on the bottom portion to detect the various parameters of the liquid within the bioreactor.

Most of the bioreactors of the present invention are injection molded, but they can be rotoformed in the case that a jacketed body is required or unique featured are added which are best accomplished via rotomolding techniques.

An additional advantage to a molded or rigid formed plastic body is that heating or cooling blankets can be easily attached to them.

In practice, the body is designed as desired, preferably with a substantially flat open rim one circular sidewall extending downwardly from the rim and terminating in a rounded bottom as shown in FIG. 1. The body is preferably made of molded plastic such as polystyrene, preferably with some or all of the desired ports, including one or more ports formed in the sidewall and more preferably with one or more ports formed in the sidewall at a level below the anticipated liquid/air level. The top is separately molded with some or all of its desired ports being molded in place. In many molding applications the ports will actually contain flash or be closed off by a thin plastic layer that needs to be removed in order to open up the ports. Alternatively, as discussed above, the ports may be formed after molding by drilling holes at the appropriate places and adding port fittings in place in a liquid tight manner.

Caps such as various Luer fittings including threaded caps, Luer based septum covers, Luer Lok caps, closed Luer or other threaded caps, plugs, tubes attached to the ports formed with hose barb fittings and the like are attached to the one or more ports.

If used, the stirrer shaft 40 with impeller(s) 42 is inserted into the port 30 in the top 16 and the bottom of the shaft 40 is centered and retained within hub 50. The top 16 is then sealed to the body 22 such as by the clips 24 or by heat sealing or adhesive.

Depending upon the type of probe and the sterilization technique chosen, one or more of the probes may be added and sealed in place at this time.

The closed bioreactor is then sterilized, packaged and sent to the user.

The bioreactor may be sterilized by many different techniques. The most common would be by radiation especially gamma and to a lesser extent, beta radiation. In this embodiment, many probes are not gamma stable and would need to be aseptically assembled into the bioreactor at the user's facility.

Another method is to use gases such as ethylene oxide. In this type of sterilization, one could use the various ports to supply y the gas and then remove it from the interior of the bioreactor. This may be a dedicated port(s) or it may then be used for another purpose such as a drain or liquid/air movement.

Alternatively, the device may be sterilized by autoclaving with steam and preferably super heated steam and pressure. In this embodiment, a vent (not shown) to remove the steam would be a useful addition to one of the ports (30 or 32).

The sterile device is placed within the stand and the various connections for air, liquid, probes, sampling, etc are attached to the device at the appropriate ports. The device is filled with media to a desired level forming a liquid/air interface somewhere below where the top 16 is attached to the body 22 to leave a head space of gas as is common in such devices. At least one port 32 is below the level of the interface.

The media is then seeded with the organism to be grown, be it plant, animal cell (CHO or NSO cells for instance) virus, yeast, mold or bacteria (such as *E. coli*) and the liquid is circulated and air/gases and liquids moved into or out of the device in a manner to effectively grow the culture inside.

After a suitable time, the cells may be harvested either by drawing off the liquid, leaving the cells behind, or in the instance where the cells need to be ruptured to recover the desired product by either removing the cells and then rupturing them or rupturing them in the device and then removing the ruptured mass for further processing. Additionally, with the vast number of available ports one could use the device to run a perfusion reactor in which small amounts of cells or expressed product is removed on a continual basis for further processing while the cells within the device continue to grow and make the desired product.

Once the process is completed the device is drained and all connections removed and the device ports are sealed. It is then disposed of properly such as by incineration.

What is claimed:

1. A bioreactor for culturing, fermenting or processing a biomass consisting of: a presterilized, disposable housing made of a rigid plastic, said housing having a top and a body releasably sealed to each other, wherein the top and body are sealed to each other by a gasket interposed between the top and body and a mechanical means for releaseably holding the top and body together, the body having an interior space, a first set of one or more access ports formed in the top, the body of the housing and in fluid communication with the interior of the housing, a second set of one or more access ports formed in the body and bottom of the housing and in fluid communication with the interior of the housing, wherein at least one access port of the second set being a valved port in the bottom of the housing forming an outlet for liquid in the housing, and at least one access port of the second set being formed in the body of the housing, so as to allow for the introduction of liquid, probes or samplers into the interior of the body, the one or more access ports having a cap to isolate the interior space of the body from the environment and an outer wall of a bottom portion of the housing has two or more locking tabs and further comprising a stand having two or more locking features that interact with the locking tabs of the housing to hold the housing in the stand in an upright and secure manner.

2. The bioreactor of claim 1 wherein the valved port further allows for the entrance of gases into the housing by a valve selected from the group consisting of a 3 position valve and Y-shaped tube with valves on each arm of the Y to control flow between gas and liquid through the port.

3. A bioreactor for culturing, fermenting or processing a biomass consisting of: a presterilized, disposable housing made of a rigid plastic, said housing having a top and a body releaseably sealed to each other, the body having an interior space, a first set done or more access ports formed in the top of the housing, a second set of one or more access ports formed in the body and bottom of the housing and in fluid communication with the interior of the housing wherein at least one access port of the second set being a valved port in the bottom of the housing forming an outlet for liquid in the housing, and at least one access port of the second set being formed in the body of the housing and in fluid communication with the interior of the housing so as to chow for the introduction of liquid, probes or samplers into the interior of the body, the one or more access ports of the first and second set having a cap to isolate the interior space of the body from the environment, the top and body are releasably sealed to each other by a gasket interposed between the top and body and a mechanical means for holding the top and body together and wherein the mechanical means is selected from the group consisting of clips and clamps and an outer wall of a bottom portion of the housing has two or more locking tabs and further comprising a stand having two or more locking features that interact with the locking tabs of the housing when the housing is inserted into the stand to hold the housing in the stand in an upright and secure manner.

4. The bioreactor of claim 3 wherein the valved port further allows for the entrance of gases into the housing by a valve selected from the group consisting of a 3 position valve and Y-shaped to with valves on each arm of the Y to control flow between gas and liquid through the port.

* * * * *

UNITED STATES PATENT AND TRADEMARK OFFICE
CERTIFICATE OF CORRECTION

PATENT NO. : 8,999,702 B2
APPLICATION NO. : 12/387688
DATED : April 7, 2015
INVENTOR(S) : James E. Kelly, Jr. et al.

It is certified that error appears in the above-identified patent and that said Letters Patent is hereby corrected as shown below:

In the Claims

In column 8, line 58, in claim 3 delete "done" and insert -- of one --, therefor.

In column 8, line 66, in claim 3 delete "chow" and insert -- allow --, therefor.

In column 9, line 16, in claim 4 delete "to" and insert -- tube --, therefor. (First Occurrence)

Signed and Sealed this
Eighteenth Day of August, 2015

Michelle K. Lee
*Director of the United States Patent and Trademark Office*